(12) United States Patent
Clark et al.

(10) Patent No.: US 11,324,819 B2
(45) Date of Patent: May 10, 2022

(54) THERAPEUTIC VACCINE FOR HEPATITIS B VIRUS (HBV) USING THE HBV CORE ANTIGEN

(71) Applicant: UNIVERSITY OF WASHINGTON, Seattle, WA (US)

(72) Inventors: Edward Clark, Seattle, WA (US); Deborah L. Fuller, Seattle, WA (US); Che-Leung Law, Seattle, WA (US); Amanda Mak, Seattle, WA (US)

(73) Assignees: University of Washington, Seattle, WA (US); Abacus Bioscience, Inc., Sammamish, WA (US)

( * ) Notice: Subject to any disclaimer, the term of this patent is extended or adjusted under 35 U.S.C. 154(b) by 311 days.

(21) Appl. No.: 16/088,386

(22) PCT Filed: Nov. 22, 2016

(86) PCT No.: PCT/US2016/063246
§ 371 (c)(1),
(2) Date: Sep. 25, 2018

(87) PCT Pub. No.: WO2017/176319
PCT Pub. Date: Oct. 12, 2017

(65) Prior Publication Data
US 2020/0306367 A1 Oct. 1, 2020

Related U.S. Application Data

(60) Provisional application No. 62/319,160, filed on Apr. 6, 2016.

(51) Int. Cl.
*A61K 39/00* (2006.01)
*A61K 39/29* (2006.01)
(Continued)

(52) U.S. Cl.
CPC .... *A61K 39/292* (2013.01); *A61K 39/001129* (2018.08); *A61K 39/39* (2013.01);
(Continued)

(58) Field of Classification Search
None
See application file for complete search history.

(56) References Cited

U.S. PATENT DOCUMENTS

| 7,323,331 B2 | 1/2008 | Maki et al. |
| 2010/0119524 A1* | 5/2010 | Ulaeto .................... A61P 31/00 424/159.1 |

(Continued)

FOREIGN PATENT DOCUMENTS

| WO | 97/04000 | 2/1997 |
| WO | 2006/102408 A2 | 9/2006 |

(Continued)

OTHER PUBLICATIONS

Lobner et al., "Engineered IgG1-Fc—one fragment to bind them all," Immunological Reviews vol. 270: 113-131 (Year: 2016).*

(Continued)

*Primary Examiner* — M Franco G Salvoza
(74) *Attorney, Agent, or Firm* — McDonnell Boehnen Hulbert & Berghoff LLP

(57) ABSTRACT

Provided herein are compositions of CD1280 binding proteins and a Hepatitis B virus core antigen (HBcAg) and/or a Hepatitis B virus E antigen (HBeAg), or antigenic fragments or mutants thereof, attached to the CD180 binding protein, and methods for using the compositions to treat or limit the development of hepatitis-B virus (HBV)-related disorders.

16 Claims, 7 Drawing Sheets

Figure 2:
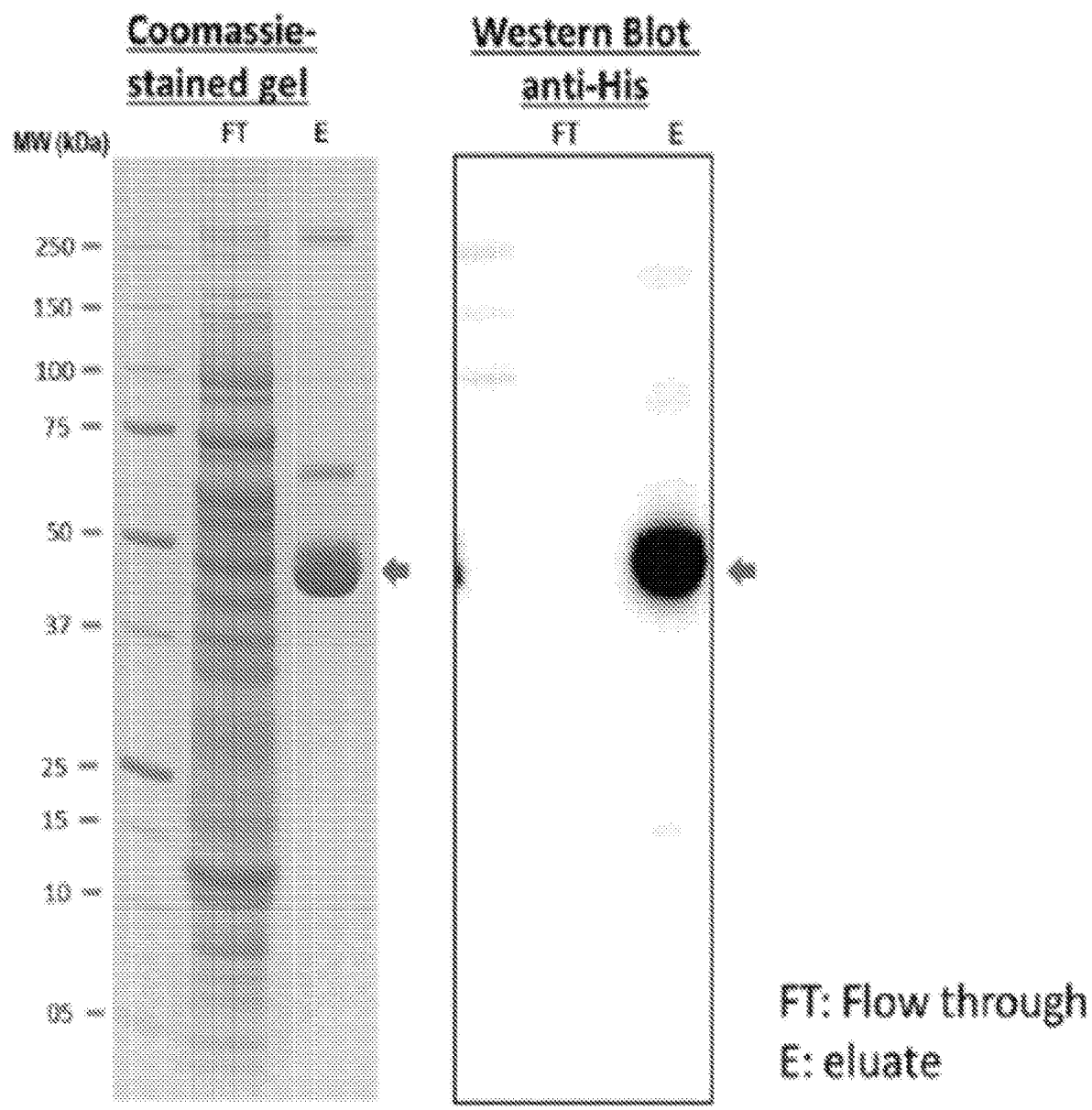

Specification includes a Sequence Listing.

(51) Int. Cl.
    *A61K 39/39*     (2006.01)
    *C07K 16/28*     (2006.01)
    *C12N 7/00*     (2006.01)

(52) U.S. Cl.
    CPC ............ *C07K 16/2896* (2013.01); *C12N 7/00* (2013.01); *C07K 2317/524* (2013.01); *C07K 2317/526* (2013.01); *C07K 2317/56* (2013.01); *C07K 2317/622* (2013.01); *C07K 2319/00* (2013.01); *C12N 2730/10134* (2013.01)

(56) References Cited

U.S. PATENT DOCUMENTS

| | | |
|---|---|---|
| 2012/0020965 A1 | 1/2012 | Chaplin et al. |
| 2013/0209395 A1 | 8/2013 | Weiner et al. |
| 2019/0249434 A1 | 8/2019 | Shiao et al. |

FOREIGN PATENT DOCUMENTS

| | | | |
|---|---|---|---|
| WO | WO-2007148924 A1 * | 12/2007 | ......... A61K 47/6923 |
| WO | 2009/036228 | 3/2009 | |
| WO | 2010/042870 A1 | 4/2010 | |
| WO | 2014/046994 A1 | 3/2014 | |

OTHER PUBLICATIONS

Buffa et al., "Evaluation of TLR Agonists as Potential Mucosal Adjuvants for HIV gp140 and Tetanus Toxoid in Mice," Plos One 7(12): e50529 (Year: 2012).*

Di Mattia et al., "Antigenic Switching of Hepatitis B Virus by Alternative Dimerization of the Capsid Protein," Structure 21(1): 133-142 (Year: 2013).*

The International Search Report (ISR) with Written Opinion for PCT/US2017/063246 dated Jan. 30, 2017, pp. 1-10.

Milich, David E. et al. "Role of B cells in antigen presentation of the hepatitis B core" Proc. Natl. Acad. Sci. (1997) vol. 94, p. 14648-14653.

Huang, Chien-Fu et al. "The Immune Response Induced by Hepatitis B Virus Principal Antigens" Cellular & Molecular Immunology (2006) vol. 3(2), pp. 97-106.

Akbar et al., MSI. HBsAg, HBcAg, and combined HBsAg/HBcAg-based therapeutic vaccines in treating chronic hepatitis B virus infection. Hepatobiliary Pancreat Dis Int. 2013. 12:363-9.

Akbar et al., Strong and multi-antigen specific immunity by hepatitis B core antigen (HBcAg)-based vaccines in a murine model of chronic hepatitis B: HBcAg is a candidate for a therapeutic vaccine against hepatitis B virus. Antiviral Res 2012;96:59-64.

Alving et al., Adjuvants for human vaccines. Curr Opin Immunol. 2012. 24:310-5.

Beck et al., Hepatitis B virus replication. World J Gastroenterol WJG, 2007. 13:48-64.

Bertoletti et al., Innate and adaptive immune responses in chronic hepatitis B virus infections: towards restoration of immune control of viral infection. Gut 2012. 61 :1754-1764.

Bourne et al., A mutant hepatitis B virus core protein mimics inhibitors of icosahedral capsid self-assembly. Biochemistry 2009. 48:1736-1742.

Cao et al., CD8+ T cell responses specific for hepatitis B virus core protein in patients with chronic hepatitis B virus infection. J Clin Virol. 2014. 61:40-6.

Chaplin et al., Targeting antigens to CD180 rapidly induces antigen-specific IgG, affinity maturation and immunologic memory. 2013. J Exp Med 210:2135-46.

Chaplin et al., Anti-CD180 (RP105) activates B cells to rapidly produce polyclonal Ig via a T cell and MyD88-independent pathway. J Immunol, 2011. 187:4199-209.

Chappell et al., Controlling immune responses by targeting antigens to dendritic cell and B cell. 2014. Int Immunol 26:3-11.

Clark et al., Activation of human B cells. Comparison of the signal transduced by IL-4 to four different competence signals. J Immunol. 1989. 143:3873-80.

Coffman et al., Vaccine adjuvants: putting innate immunity to work. Immunity. 2010. 33:492-503.

Dimattia et al., Antigenic switching of hepatitis B virus by alternative dimerization of the capsid protein. Structure. 2013. 21:133-42.

Fuller et al., Immune responses to hepatitis B virus surface and core antigens in mice, monkeys, and pigs after Accell particle-mediated DNA immunization. Ann N Y Acad Sci. 1995. 772:282-4.

Fuller et al., Therapeutic DNA vaccine induces broad T cell responses in the gut and sustained protection from viral rebound and AIDS in SIV-infected rhesus macaques. PLoS One. 2012. 7:e33715.

Gaggar et al., Safety, tolerability and immunogenicity of GS-4774, a hepatitis B virus-specific therapeutic vaccine, in healthy subjects: a randomized study, Vaccine. 2014. 32(39): 4925-31.

Gonczol et al., Development of a cytomegalovirus vaccine: lessons from recent clinical trials. Expert Opin Biol Ther. 2001. 1 :401-12.

Hebeis et al., Vav proteins are required for B-lymphocyte responses to LPS. Blood, 2005. 106:635-40.

Hebeis et al., Activation of virus-specific memory B cells in the absence of T cell help. J Exp Med 2004. 199:593-602.

Kim et al., Hepatitis B vaccination in HIV-infected adults: current evidence, recommendations and practical considerations. International journal of STD & AIDS, 2009. 20:595-600.

Kim et al., Epidemiology of hepatitis B in the United States. Hepatology, 2009. 49:S28-34.

Kubba et al., Non-responders to hepatitis B vaccination: a review. Communicable disease and public health 2003. 6:106-12.

Lavanchy et al., Hepatitis B virus epidemiology, disease burden, treatment, and current and emerging prevention and control measures. J Viral Hep 2004. 11:97-107.

Liang et al., Predictors of relapse in chronic hepatitis B after discontinuation of anti-viral therapy. Aliment Pharmacol Ther, 2011. 34:344-52.

Loudon et al., GM-CSF increases mucosal and systemic immunogenicity of an H1 N1 influenza DNA vaccine administered into the epidermis of non-human primates PLoS One. 2010. 5:e11021.

LSDF Grant—NCT01779505—A Phase 1a Trial Assessing the Safety, Tolerability, and Immunogenicity of GS-4774 (GI-13020) at Various Dose Levels and Regimens in Healthy Adults, first posted Jan. 30, 2013, last update posted Jan. 8, 2014, accessed Jun. 28, 2019, pp. 1-6.

Luckhaupt et al., Deaths due to bloodborne infections and their sequelae among health-care workers. Am J Ind Med. 2008. 51: 812-24.

Ma et al., CD22 is required for protection against West Nile Virus infection. J Virol. 2013. 87:3361-75.

Maini et al., The role of virus-specific CD8(+) cells in liver damage and viral control during persistent hepatitis B virus infection. J Exp Med 2000;191:1269-1280.

Menendez-Arias et al., Nucleoside/nucleotide analog inhibitors of hepatitis B virus polymerase: mechanism of action and resistance. Curr Opin Virol. 2014. 8:1-9.

Mitchell et al., The increasing burden of imported chronic hepatitis B—United States, 197 Apr. 2008. PLoS One. 2011. 6:e27717.

Miyake et al., cell proliferation and protection from apoptosis with an antibody against a 105-kD molecule: unresponsiveness of X-linked immunodeficient B cells. J Exp Med 1994. 180:1217-24.

Miyake et al., RP105, a novel B cell surface molecule implicated in B cell activation, is a member of the leucine-rich repeat protein family. J Immunol 1995. 154:3333-40.

Moxon et al., The next decade of vaccines: societal and scientific challenges. Lancet. 2011. 378:348-59.

Ott et al., Global epidemiology of hepatitis B virus infection: new estimates of age-specific HBsAg seroprevalence and endemicity. Vaccine 2012. 30:2212-9.

Oyston et al., The current challenges for vaccine development. J Med Microbiol. 2012. 61 :889-94.

Packianathan et al., Conformational changes in the hepatitis B virus core protein are consistent with a role for allostery in virus assembly. J Virol. 2010. 84:1607-1615.

(56) References Cited

OTHER PUBLICATIONS

Penna et al., Cytotoxic T lymphocytes recognize an HLA-A2-restricted epitope within the hepatitis B virus nucleocapsid antigen. J Exp Med. 1991. 174:1565-70.

Perz et al., The contributions of hepatitis B virus and hepatitis C virus infections to cirrhosis and primary liver cancer worldwide. J Hepatol 2006. 45:529-38.

Ramos et al., RIG-I like receptors and their signaling crosstalk in the regulation of antiviral immunity. Curr Opin Virol, 2011. 1:167-176.

Rappuoli et al., Vaccines for the twenty-first century society. Nat Rev Immunol. 2011. 11:865-72.

Roberts et al., Clinical safety and efficacy of a powdered Hepatitis B nucleic acid vaccine delivered to the epidermis by a commercial prototype device. Vaccine. 2005. 23:4867-78.

Roy et al., Induction of antigen-specific CD8+ T cells, T helper cells, and protective levels of antibody in humans by particle-mediated administration of a hepatitis B virus DNA vaccine. Vaccine. 2001. 19:764-78.

Shimazu et al., MD-2, a molecule that confers lipopolysaccharide responsiveness on Toll-like receptor 4. J Exp Med 1999. 189:1777-82.

Sun et al., A new unconventional HLA-A2-restricted epitope from HBV core protein elicits antiviral cytotoxic T lymphocytes. Protein Cell. 2014. 5:317-27.

Suthar et al., West Nile virus infection and immunity. 2013. Nat Rev Microbiol 11:115-128.

Swain et al., Tolerability and immune responses in humans to a PowderJect DNA vaccine for hepatitis B. Dev Biol. 2000 104:115-119.

Thai et al., Convergence and coevolution of hepatitis B virus drug resistance. Nat Commun. 2012. 3:789.

Valentine et al., Antibody to a novel 95-kDa surface glycoprotein on human B cells induces calcium mobilization and B cell activation. J Immunol. 1988. 140:4071-8.

Vandepapeliere et al., Therapeutic vaccination of chronic hepatitis B patients with virus suppression by antiviral therapy: a randomized, controlled study of co-administration of HBsAg/AS02 candidate vaccine and lamivudine. Vaccine 2007. 25:8585-8597.

Wang et al., Immunotherapeutic interventions in chronic hepatitis B virus infection: a review. J Immunol Methods. May 2014;407:1-8.

Wasley et al., The prevalence of hepatitis B virus infection in the United States in the era of vaccination. J Infect Dis. 2010. 202:192-201.

Wiegand et al., Management of chronic hepatitis B: status and challenges beyond treatment guidelines. Semin Liver Dis. 2010;30:361-377.

Weinbaum et al., Recommendations for identification and public health management of persons with chronic hepatitis B virus infection. Centers for Disease Control and Prevention (CDC). MMWR Recomm Rep. 2008. 57 (RR-8):1-20.

World Health Organization—Hepatitis B vaccines. Releve epidemiologique hebdomadaire I Section d'hygiene du Secretariat de la Societe des Nations = Weekly epidemiological record/ Health Section of the Secretariat of the League of Nations, 2004. 79:253-64.

Yazawa et al., CD19 regulates innate immunity by the toll-like receptor RP105 signaling in B lymphocytes. Blood, 2003. 102:1374-80.

Jia, et al. "Hepatitis B Virus Core Protein Sensitizes Hepatocytes to Tumor Necrosis Factor-Induced Apoptosis by Suppression of the Phosphorylations of Mitogen-Activated Protein Kinase Kinase 7," "Journal of Virology", vol. 89, Issue 4, pp. 2041-2051.

Core protein [Hepatitis B virus], Shen, T. et al., "GenBank", ABY65436.1, Nov. 2007.

\* cited by examiner

G28-8LH-HBcAgY132A-His for mammalian cell expression

| L | G28-8VL | GS | G28-8VH | GS | HBcAgY132A | H |

L: leader sequence from G28-8 VL
G28-8VL: Light chain variable domain of G28-8
GS: (Gly4Ser)4 linker
G28-8VH: Heavy chain variable domain of G28-8
HBcAgY132A: HBV core antigen amino acid 1-149 with tyrosine (Y) at position 132 replaced by alanine (A)
H: 6x His tag

FIGURE 1

_US 11,324,819 B2_

THERAPEUTIC VACCINE FOR HEPATITIS B VIRUS (HBV) USING THE HBV CORE ANTIGEN

CROSS REFERENCE

This application is a U.S. national phase of International Application No. PCT/US2016/063246, filed on Nov. 22, 2016, which claims priority to U.S. Provisional Application No. 62/319,160, filed Apr. 6, 2016, both of which are incorporated by reference herein in their entirety.

STATEMENT OF GOVERNMENT RIGHTS

This invention was made with government support under AI044257 awarded by the National Institutes of Health. The US Government has certain rights in this invention.

BACKGROUND OF THE INVENTION

In spite of the availability of prophylactic Hepatitis B virus (HBV) vaccines, HBV infection remains a very significant global health problem in both industrialized and developing nations; it is second only to tobacco as a cause of cancer. There is a clear unmet need for a therapeutic HBV vaccine for patients chronically infected with HBV (CHB). 10-30% of those vaccinated with marketed HBV vaccines do not respond either due to genetic factors, or non-compliance (failure to return for a series of 3 vaccinations). Only 37% of individuals vaccinated once with a licensed HBV vaccine are protected; even after three vaccinations, which are difficult to achieve, many people do not respond effectively. There is no effective vaccine for the 400 million people chronically infected with HBV, including asymptomatic HBV carriers. The drugs currently used to treat CHB patients are problematic. Sustained antiviral responses are rarely achieved and the currently available therapies can lead to viral resistance and produce side effects in many CHB patients.

SUMMARY OF THE INVENTION

In one aspect, the invention provides compositions, comprising:
  (a) a CD180 binding protein; and
  (b) a Hepatitis B virus core antigen (HBcAg) and/or a Hepatitis B virus E antigen (HBeAg), or antigenic fragments or mutants thereof, attached to the CD180 binding protein.

In one embodiment, the CD180 binding protein is an anti-CD180 antibody or antibody fragment, such as an anti-CD180 monoclonal antibody or antibody fragment. In another embodiment, the CD180 binding protein comprises a single chain (sc) recombinant protein, wherein the sc recombinant protein comprises:

(i) a variable heavy (VH) chain region of an anti-CD180 antibody; and (ii) a variable light (VL) chain region of an anti-CD180 antibody;

wherein the HBcAg and/or the HBeAg is located at the N-terminus or the C-terminus of the sc recombinant protein.

In one embodiment, the VH and VL chain regions are from an anti-human CD180 antibody, such as an anti-human CD180 monoclonal antibody. In another embodiment, the sc recombinant protein does not include any other immunoglobulin domains. In a further embodiment, the sc recombinant protein further comprises:

(iii) CH2 and CH3 domains from an immunoglobulin (Ig), such as a human Ig, or functional mutants thereof, wherein the CH2 and CH3 domains are located C-terminal to the VH and VL domains.

For example, the sc recombinant protein may comprise CH2 and CH3 domains from IgG1, such as human IgG1, or functional mutants thereof. In one embodiment, the VL chain region is located N-terminal to the VH chain region. In another embodiment, the VH chain region is located N-terminal to the VL chain region. In a further embodiment, the CD180 binding protein competes for binding to CD180 with monoclonal antibody G28-8.

In another embodiment, the HBcAg and/or the HBeAg is/are capable of multimerizing, such as dimerizing. In one embodiment, the HBcAg and/or the HBeAg comprise a multimerization domain, such as a dimerization domain. In various further embodiments, the HBcAg and/or the HBeAg comprises a polypeptide at least 90% identical over its length to the amino acid sequence of SEQ ID NO:13, 14, 15, 16, or 17. In a further embodiment, the composition comprises a polypeptide at least 90% identical over its length to the amino acid sequence of SEQ ID NO:2, 3, 5, 6, 8, 9, 11, 12, 18, 19, 20, or 21.

In one embodiment, the composition further comprises an adjuvant, including but not limited to toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

In further aspects, the invention provides isolated nucleic acids encoding a composition of any embodiment or combination of embodiments of the invention, expression vectors comprising the isolated nucleic acids of the invention operatively linked to a suitable control sequence, and recombinant host cell comprising the expression vectors of the invention.

In another aspect, the invention provides pharmaceutical compositions comprising the composition, isolated nucleic acid, or expression vector of any embodiment, in combination with a pharmaceutically acceptable carrier.

In a further aspect, the invention provides methods for treating or limiting the development of a hepatitis-B virus (HBV)-related disorder, comprising administering to an individual in need thereof an amount effective to treat or limit development of the HBV-related disorder of the composition, isolated nucleic acid, expression vector, or the pharmaceutical composition of any embodiment of the invention.

BRIEF DESCRIPTION OF THE FIGURES

FIG. 1. Design of G28-8LH-HBcAg-Y132A-His protein.

FIG. 2. Characterization of recombinant G28-8LH-HBcAgY132A-His. G28-8LH-HBcAgY132A-His was transiently expressed in CHO cells. Culture supernatant was passed over a Ni2+ affinity chromatography column. Bound G28-8LH-HBcAgY132A-His was eluted with imidazole. Eluted protein (E) was characterized by reducing SDS-PAGE and western blotting using an anti-6×-His sera.

FIG. 3. Binding of recombinant G28-8LH-HBcAgY132A-His to human B cells detected by flow cytometry. A Direct binding to human CD20+ tonsillar B cells. B Competition binding assay between G28-8LH-HBcAgY13A-His and FITC-labeled parent G28-8 antibody.

FIG. 4. Recombinant G28-8LH-HBcAgY132A-His activates human B cells. Er-human blood mononuclear cells enriched for B cells were incubated either with media (black line), G28-8 (dotted line), or LH-HBcAgY132A-His (dashed line). Samples were analyzed 24 hours later for CD20 and CD40 expression using flow cytometry. Graph shows CD40 expression of gated CD20+ B cells.

Figure 5:
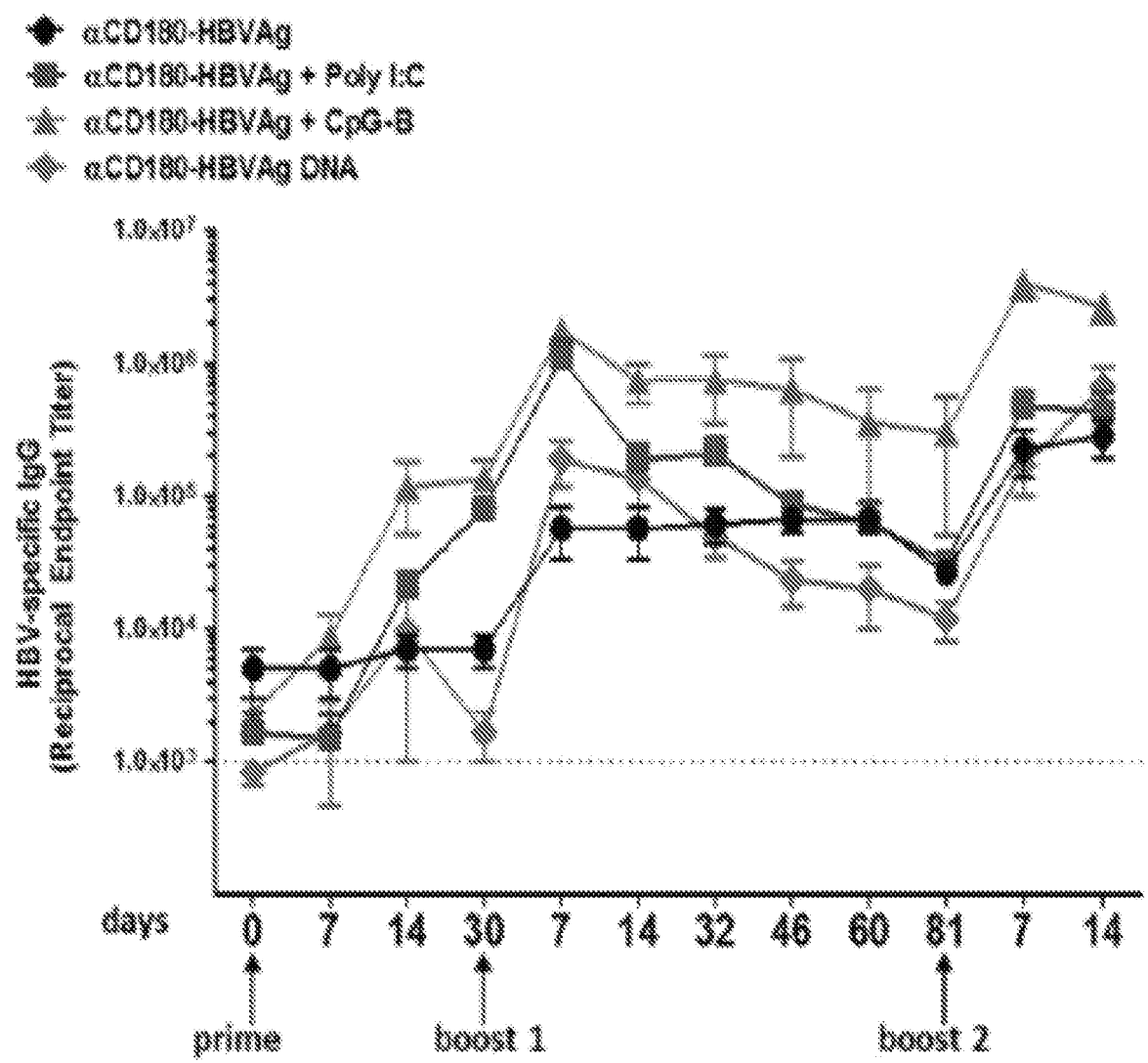
Figure 6:
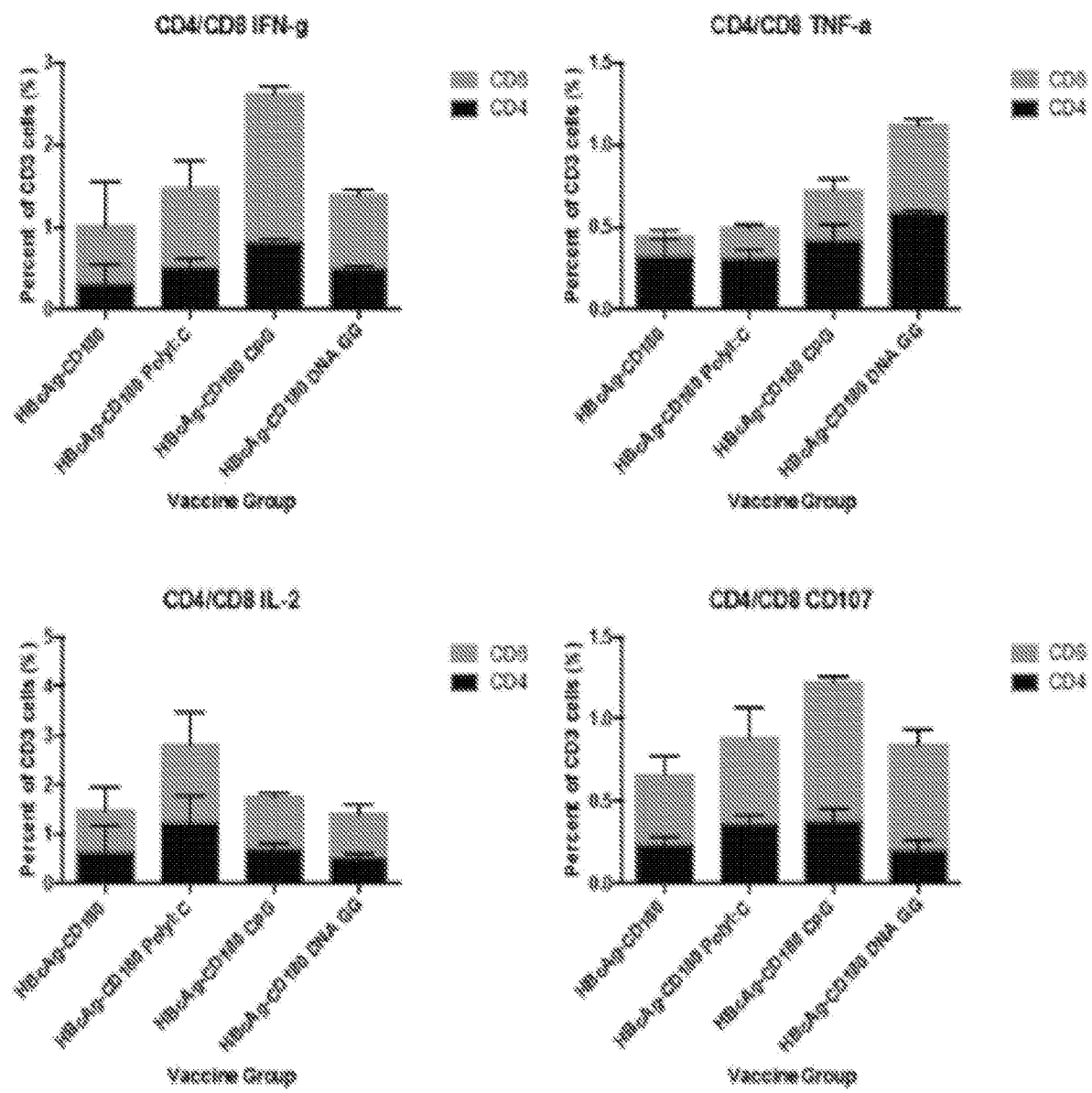

FIG. 5. IgG Antibody responses in macaques immunized and boosted with recombinant G28-8LH-HBcAgY132A-His vaccine (aCD180-HBVAg). Groups of rhesus macaques (*Macaca mulatta*) (N=3) were vaccinated subcutaneously with either: 1) G28-8LH-HBcAgY132A-His (aCD180-HBVAg); 2) G28-8LH-HBcAgY132A-His (aCD180-HBVAg) plus 1 mg long chain poly I:C; G28-8LH-HBcAgY132A-His (aCD180-HBVAg) plus CpGB; or 4) G28-8LH-HBcAgY132A-His encoding plasmid DNA (αCD180-HBVAg DNA) by delivering the DNA directly into cells of the skin using a gene gun. Animals were vaccinated on days 0, 30 and 81, and on days 0, 7, 14, 30 (time of first boost), 44, 62, 76, 90, 111 (time of second boost) 118, 125, 139 and 164 serum samples were obtained and evaluated for HBcAg-specific IgG antibody levels using ELISA. Endpoint titers are shown on a log scale.

FIG. 6. CD8 T cell responses in macaques immunized and boosted with recombinant G28-8LH-HBcAgY132A-His vaccine (HBcAg-CD180) detected by intracellular cytokine staining. Groups of rhesus macaques (*Macaca mulatta*) (N=3) were vaccinated as described in FIG. 5 and 28 days after the second booster immunization, heparinized blood samples were obtained, from which PBMCs were isolated. PBMCs were incubated with HBcAg peptide pools. Cells were then stained with mAb specific for surface markers, followed by staining for intracellular cytokines. Fixed cells were then analyzed by multicolor flow cytometry. Shown for each of the four vaccinated groups are CD3+CD4+ T cells (black) or CD3+CD8+ T cells (gray) expressing either IFN-γ, TNF-α, IL-2 or CD107.

FIG. 7. HBcAg coupled to anti-CD180 (G28-8LH-HBcAgY132A-His) induces a strong IgG antibody response but free HBcAgY123A does not. Two groups of rhesus macaques (*Macaca mulatta*) (N=3) were immunized on day 0 and day 30 via the subcutaneous route with either 300 mg recombinant G28-8LH-HBcAgY132A-His in 1 ml (black) or an equivalent amount of HBcAgY132A (150 mg) in 1 ml (white) and bled day 0 before immunization and 14 days after the second immunization. Sera were then assessed for IgG antibodies to HBcAgY132A using ELISA using 96 well plates coated with 200 ng/well recombinant HBcAgY132A, serial dilutions of serum samples starting with a 1:1000 dilution and an HRP-anti-macaque IgG second step.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the present invention provides compositions, comprising:

(a) a CD180 binding protein; and (b) Hepatitis B virus core antigen (HBcAg) and/or Hepatitis B virus E antigen (HBeAg), or antigenic fragments or mutants thereof, attached to the CD180 binding protein.

The compositions of the invention can be used, for example, to induce prophylactic responses in individuals at risk of HBV infection, and therapeutic responses in already infected individuals and in immunodeficient individuals who do not respond well to standard vaccines. The present invention is highly significant because it provides a therapeutic vaccine for one of the major causes of cancer and liver disease in the world: hepatitis B virus (HBV). HBV infection is a serious global public health problem in both industrialized and developing nations. 10-30 million people worldwide become infected with HBV each year, and more than 2 billion people worldwide have been infected with HBV. Significantly, the ability of unvaccinated individuals to mount effective immune responses against HBV is correlated with age. Infants and young children are particularly at risk, as 90% of infants and up to 50% of young children infected with HBV ultimately develop chronic infections. About 400 million are chronically infected with HBV (CHB), and in the USA there are approximately 1.4 million CHB infected people[5]. In the USA the prevalence of HBV while dropping in children, has changed little in adults[11] such that the burden of chronic hepatitis B among adults remains large[6]; in some groups it is as high as 1%. An estimated 1 million people die each year from hepatitis and its complications, including about 5,000 people in the US. Of the 5000 persons in the United States who die each year from HBV related conditions, 300 die from fulminant hepatitis; 3-4000, from cirrhosis; and 600-1000, from primary hepatocellular carcinoma (HCC). In the US, approximately 400 health care workers are infected each year and are at risk from dying from HBV-related disease[16].

The CD180 binding protein may be any molecule that binds directly to CD180 present in the surface of B cells, macrophages, or dendritic cells. In various non-limiting embodiments, the CD180 binding protein may be a peptide mimetic or an antibody.

In a particular embodiment, the CD180 binding protein an antibody or antibody fragment. As used herein, "antibody" includes reference to an immunoglobulin molecule immunologically reactive with human CD180 (preferably selective for CD180), and includes monoclonal antibodies. Various isotypes of antibodies exist, for example IgG1, IgG2, IgG3, IgG4, and other Ig, e.g., IgM, IgA, IgE isotypes. The term also includes genetically engineered forms such as chimeric antibodies (e.g., humanized murine antibodies) and heteroconjugate antibodies (e.g., bispecific antibodies), fully humanized antibodies, and human antibodies. As used throughout the application, the term "antibody" includes fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) Biochemistry 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. Various antigen binding domain-fusion proteins are also disclosed, e.g., in US patent application Nos. 2003/0118592 and 2003/0133939, and are encompassed within the term "antibody" as used in this application.

An antibody immunologically reactive with human CD180 can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In one embodiment, the CD180 binding protein comprises a single chain (sc) recombinant protein, wherein the sc recombinant protein comprises:

(i) a variable heavy (VH) chain region of an anti-CD180 antibody; and (ii) a variable light (VL) chain region of an anti-CD180 antibody.

The VH and VL chain regions may be from an anti-human CD180 antibody, such as an anti-human CD180 monoclonal antibody. Exemplary commercially available CD180 anti-human monoclonal antibodies from which the VH and VL chains may be used include, but are not limited to, those sold by AbD Serotec ("MHR73"), BD Biosciences, Thermo Scientific, Sigma Aldrich, etc.), ("G28-8"), and LifeSpan ("200.1"). In one embodiment, the single chain recombinant protein does not include any other immunoglobulin domains (i.e.: a single chain variable fragment (scFv). In an alternative embodiment, the single chain recombinant protein further comprises: CH2 and CH3 domains from an immunoglobulin (Ig), such as a human Ig, or functional mutants thereof, wherein the CH2 and CH3 domains are located C-terminal to the VH and VL domains. The CH2 and CH3 domains may be from any immunoglobulin as deemed appropriate for an intended use of the composition, including but not limited to IgA1, IgA2, IgG1, IgG2, IgG3, IgG4, IgM, etc. In a particular embodiment, the sc recombinant protein comprises CH2 and CH3 domains from IgG1, such as human IgG1, or functional mutants thereof. In a particular embodiment, such "functional mutants" comprise CH2 and/or CH3 domains that have impaired binding to human or animal Fc receptor FcγRIIb and/or to human or animal complement proteins; the Fc domain of the recombinant molecules is an altered human IgG1 Fc domain with three amino acid changes (P238S, P331S, K322S) that reduce the binding of the molecule to Fc receptors and C1q. Other amino acid substitutions that can reduce binding of human IgG1 to various Fc receptors have been reported (J Biol Chem 276: 6591-6604), including but not limited to E233P, L234V, L235A, G236 deletion, P238A, D265A, N297A, A327Q, and P329A. Substitutions at these amino acids reduce binding to all FcγR (J Biol Chem 276: 6591-6604). Substitutions at D270A, Q295A, or A327S reduce binding to FcγRII and FcγRIIIA (J Biol Chem 276: 6591-6604). Substitutions at S239A, E269A, E293A, Y296F, V303A, A327G, K338A, and D376A reduce binding to FcγRIIIA but not FcγRII (J Biol Chem 276: 6591-6604). A combination of two of more of these substitutions can be engineered in the Fc domains of human IgG1 to achieve the desired effects on inhibiting Fc-FcγR interaction between CD180 targeted vaccines and FcgR expressing cells. Similarly, modifying the glycosylation profile of human IgG1, for example, substitution of the N-linked glycosylation site at Asn-297 of human IgG1, eliminates N-linked glycosylation of human IgG1, thereby eliminating its binding to Fc receptors as well as complement fixation functions (John S. Axford (ed.), Glycobiology and Medicine, 27-43; 2005 Springer.

In these various embodiments of the compositions of the invention, the VL chain region may be located N-terminal to the VH chain region, or the VH chain region may be located N-terminal to the VL chain region, as disclosed in the examples that follow.

In one embodiment, the CD180-antibody comprises mAb G28-8, which is commercially available from a number of sources, (BD Biosciences, Thermo Scientific, Sigma Aldrich, etc.), a F(ab')2 fragment of mAb G28-8, or a single chain recombinant protein having the VL and VH domains of G28-8, and optionally further comprising CH2 and CH3 domains from an immunoglobulin (Ig), such as a human Ig, or functional mutants thereof. The inventors have used a variety of such G28-8 based compositions in the examples herein to demonstrate activity of the compositions of the invention.

In another embodiment, the CD180 binding protein competes for binding to CD180 with monoclonal antibody G28-8. As used herein, competing CD180 binding proteins are those binding proteins that bind to about, substantially or essentially the same, or even the same, epitope as G28-8. Competing binding proteins, such as competing antibodies or derivatives thereof, include binding proteins with overlapping epitope specificities. Competing binding proteins are thus able to effectively compete with G28-8 antibody, such as the G28-8 antibody obtained from Thermo Scientific (the "reference antibody") for binding to CD180. A binding protein that competes with the reference G28-8 antibody for binding to CD180 will be able to effectively or significantly reduce (i.e.: reduce by at least 10%; preferably by at least 20%, 30%, 40%, 50%, 60%, 70%, 80%, 90%, or more) reference G28-8 antibody binding to CD180, as evidenced by a reduction in bound label. In one embodiment, the reference G28-8 antibody is pre-mixed with varying amounts of the test binding proteins (e.g., 1:10, 1:100 or 1:1000) for a period of time prior to applying to a CD180 composition. In other embodiments, the reference G28-8 antibody and varying amounts of test binding proteins can simply be admixed during exposure to the CD180 composition. By using species or isotype secondary antibodies one will be able to detect only the bound reference G28-8 antibody, the binding of which will be reduced by the presence of a test binding protein that "competes" for binding. Detection of such binding events is well understood by those of skill in the art; examples are provided herein. For a further example, see Otipoby K L, Nagai Y, Shu G L, Miyake K, Clark E A. CD180 (RP105/Bgp95) workshop report. In Leukocyte Typing VII. White Cell Differentiation Antigens. Eds. D. Y. Mason et al., Oxford University Press, BC7, pp. 120-123, 2002.

As the identification of competing binding proteins is determined in comparison to the reference G28-8 antibody, it will be understood that actually determining the epitope to which the binding proteins bind is not in any way required in order to identify a competing binding proteins. However, epitope mapping can be performed using standard techniques, if desired.

The compositions of the invention comprise a Hepatitis B virus core antigen (HBcAg) and/or a Hepatitis B virus E antigen (HBeAg)), or antigenic fragments or mutants thereof (collectively referred to as HBcAg and/or HBeAg), attached to the CD180 binding protein. Thus, the compositions may comprise one or more HBeAgs and/or one or more HBeAgs. In all embodiment, one or more copies of HBcAgs and/or HBeAgs may be present at the N-terminus or the C-terminus of the single chain recombinant protein.

In one embodiment, the HBcAg and/or the HBeAg is capable of multimerizing (i.e.: forming dimers, trimers, tetramers, or other multimers). In a particular embodiment, the HBcAg and/or HBeAg are capable of dimerizing. In this embodiment, the HBV antigen forms the dimer in the composition. Recombinant proteins comprising HBeAg or wildtype HBcAg and dimeric anti-CD180 antibody or antibody fragments likely cannot be expressed efficiently. Thus, the inventors have used HBeAG and/or HBcAg that can form dimers, greatly enhancing efficient expression of the recombinant proteins of the invention. Furthermore, this design makes it (a) unnecessary to include a hinge region in the composition (as in a scAb) to create a dimer, and (b) acceptable to have a composition containing VL and VH only without any Fc domains, thereby reducing the risk of Fc-mediated depletion of the CD180-expressing antigen-presenting cells.

In one such embodiment, the HBcAg and/or HBeAg are capable of multimerization without the addition of an exogenous multimerization domain. For example, the HBV e-antigen (HBeAg), while being very closely related to HBcAg retains a propeptide that both blocks its interactions with HBcAg and enables it to form a loop structure and dimers. As a result, unlike HBcAg, HBeAg is capable of multimerizing, does not form capsids and is secreted from cells. In another embodiment, an HBcAg mutant having a single amino acid substitution of tyrosine to alanine at position 132 (HBcAgY132A) prevents the assembly of HBcAgY132A into higher order capsids. Instead, HBcAgY132A is expressed as a dimer. In a further embodiment, the HBcAg and/or the HBeAg comprise a multimerization domain, such as a dimerization domain. In these embodiments, the compositions do not form large, virus-like particles. Non-limiting examples of the numerous dimerization domains known to those of skill in the art and suitable for use in the present invention include, but are not limited to peptide helices containing at least one helix, or a structure formed by a helix, a coil and another helix, etc., coiled coil structures, dimerization domains within, for example, many cell surface signaling receptors, Fc regions or hinge regions of an antibody, leucine zippers, the STAT protein N terminal domain, FK506 binding protein, the LexA protein C-terminal domain, nuclear receptors, the FkpA N-terminal domain, orange carotenoid protein from *A. maxima*, M1 matrix protein from influenza, neuraminidase from influenza virus, *E. coli* fuculose aldolase; and the like. (see, e.g., O'Shea, Science. 254: 539 (1991), Barahmand-Pour et al., Curr. Top. Microbiol. Immunol. 211: 121-128 (1996); Klemm et al., Annu. Rev. Immunol. 16: 569-592 (1998); Klemm et al., Annu. Rev. Immunol. 16: 569-592 (1998); Ho et al., Nature. 382: 822-826 (1996); and Pomeranz et al., Biochem. 37: 965 (1998)). Further examples include residues 325 to 410 in the bovine papillomavirus E2 protein, (Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514), Type I deiodinase (D1): DFLVIYIEEAH-ASDGW (SEQ ID NO: 7) or ADFL—YI-EAH-DGW (SEQ ID NO: 63); HIV-1 Capsid Protein: QGPKEP-FRDYVDRFYKTLRA (SEQ ID NO: 10); leucine zipper dimerization motif of yeast GCN4: HMKQL D VEEL S NYHL N VARL K VGER (SEQ ID NO: 22); leucine zipper in *Escherichia coli* transcriptional antiterminator protein; BgIG: GVTQLMREMLQLIKFQFSLNYQEESL-SYQRLVT (SEQ ID NO: 23), EVSALEK (SEQ ID NO: 24) and/or KVSALKE (SEQ ID NO: 25).

In embodiments where the composition comprises HBcAg, the composition may comprise an HBcAg polypeptide at least 90% identical over its length to the amino acid sequence of SEQ ID NO:13, 14, 15, or 16.

```
Full length HBcAg amino acid 1-179
                                                      SEQ ID NO: 13
  1   MDIDPYKEFG  ASVELLSFLP  SDFFPSIRDL  LDTASALYRE  ALESPEHCSP  HHTALRQAIL

61   CWGELMNLAT  WVGSNLEDPA  SRELVVSYVN  VNMGLKIRQL  LWFHISCLTF  GRETVLEYLV

121   SFGVWIRTPP  AYRPPNAPIL  STLPETTVVR  RRGRSPRRRT  PSPRRRRSQS  PRRRRSQSR

Full length HBcAg amino acid 1-179 with Y132A substitution
                                                      SEQ ID NO: 14
  1   MDIDPYKEFG  ASVELLSFLP  SDFFPSIRDL  LDTASALYRE  ALESPEHCSP  HHTALRQAIL

61   CWGELMNLAT  WVGSNLEDPA  SRELVVSYVN  VNMGLKIRQL  LWFHISCLTF  GRETVLEYLV

121   SFGVWIRTPP  AARPPNAPIL  STLPETTVVR  RRGRSPRRRT  PSPRRRRSQS  PRRRRSQSR

Short HBcAg amino acid 1-149
                                                      SEQ ID NO: 15
  1   MDIDPYKEFG  ASVELLSFLP  SDFFPSIRDL  LDTASALYRE  ALESPEHCSP  HHTALRQAIL

61   CWGELMNLAT  WVGSNLEDPA  SRELVVSYVN  VNMGLKIRQL  LWFHISCLTF  GRETVLEYLV

121   SFGVWIRTPP  AYRPPNAPIL  STLPETTVV
```

-continued

Short HBcAg amino acid 1-149 with Y132A substitution

SEQ ID NO: 16

```
  1 MDIDPYKEFG ASVELLSFLP SDFFPSIRDL LDTASALYRE ALESPEHCSP HHTALRQAIL

61 CWGELMNLAT WVGSNLEDPA SRELVVSYVN VNMGLKIRQL LWFHISCLTF GRETVLEYLV

121 SFGVWIRTPP AARPPNAPIL STLPETTVV
```

In various further embodiments, the composition may comprise an HBcAg polypeptide at least 91%, 92%, 93%, 94%, 95%, 96%, 97%, 98%, 99%, or 100% identical over its length to the amino acid sequence of SEQ ID NO:13, 14, 15, or 16. In various embodiments, additional HBcAg mutations may include (alone or in combination): F97L (J Virol. 2004 September; 78(17):9538-43), V124W (J Virol. 2013 March; 87(6):3208-16), substitution of residues that are phosphorylated in vivo, such as Ser87, Ser155, Ser162 and/or Ser170, to non-phosphorylatable residues (such as alanine or valie) (Biochem J. 2008 Nov. 15; 416(1):47-54; Biochem J. 2006 Sep. 1; 398(2):311-7), and/or substitution of one or more Cys residues (i.e.: Cys48, Cys61, Cys107, and/or Cys185) (to, for example, serine, alanine, or valine) which may increase dimerization (J Virol. 1992 September; 66(9): 5393-8).

In embodiments where the composition comprises HBeAg, the composition may comprise an HBeAg polypeptide at least 90% identical over its length to the amino acid sequence of SEQ ID NO:17.

(HBeAg)

SEQ ID NO: 17

```
S KLCLGWLWGM DIDPYKEFGA SVELLSFLPS DFFPSIRDLL

DTASALYREA LESPEHCSPH HTALRQAILC WGELMNLATW
```

-continued

```
VGSNLEDPAS RELVVSYVNV NMGLKIRQLL WFHISCLTFG

RETVLEYLVS FGVWIRTPPA YRPPNAPILS TLPETTVV
```

In various further embodiments, the composition may comprise an HBeAg polypeptide at least 91%, 92%, 93%, 94%, 95%, 96%, 97%, 98%, 99%, or 100% identical over its length to the amino acid sequence of SEQ ID NO: 17.

In all of these embodiments, the composition may further comprise an amino acid linker position between the CD180 binding protein and the HBcAg and/or HBeAg. The linker may be of any suitable length and amino acid composition, depending on the intended use. In one embodiment, the linker is between about 2-40 amino acids in length. In other embodiments, the linker may be between 10-30 or 15-25 amino acids in length. In another embodiment, the linker may be a linker rich in glycine and serine residues. In one specific embodiment, the linker may comprise the amino acid sequence

```
                                   (SEQ ID NO: 4)
         GGGGSGGGGSGGGGSGGGGS.
```

In various further embodiments, the composition may comprise or consist of a polypeptide at least 90% identical over its length to the amino acid sequence of SEQ ID NO:2, 3, 5, 6, 8, 9, 11, 12, 18, 19, 20, or 21.

G28-8LH-HBcAgY132A-His Protein

SEQ ID NO: 2

1 METPAQLLFL LLLWLPDTTG DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSG GGGSGGGGSG GGGSGGGGS*M DIDPYKEFGA*

301 *SVELLSFLPS DFFPSIRDLL DTASALYREA LESPEHCSPH HTALRQAILC WGELMNLATW*

361 *VGSNLEDPAS RELVVSYVNV NMGLKIRQLL WFHISCLTFG RETVLEYLVS FGVWIRTPPA*

421 *ARPPNAPILS TLPETTVV*(HH HHHH)

1-20: Leader
Bold: G28-8VL
Underlined: Gyl-Ser linkers
Bold and underlined: G28-8VH
Italicized and underlined: HBcAgY132A
C-terminus: 6xHis G28-8LH-HBcAgY132A-His Mature Protein (leader sequence removed from SEQ ID NO: 2)

```
                                              SEQ ID NO: 3
  1 DIQMTQSPAS LSASVGETVT ITCRASEKIY SYLAWYQQKQ GKSPQLLVYN AKTLAEGVPS

61 RFSVSGSGTQ FSLRINSLQP EDFGTYYCQH HFGSPRTFGG GTKLEIKDL G

GGGSGGGGSG
```

-continued

```
121 GGGSGGGGST GEVQLQQSGP ELVKPGASMK ISCKASGYSF TGYTMNWVKQ SHGKTLEWIG

181 LINPYNGVTS YNQKFKDKAT LTVDKSSSTA YMELLSLTSE DSAIYYCARD YNYDYFDYWG

241 QGTTLTVSSG GGGSGGGGSG GGGSGGGGSM DIDPYKEFGA SVELLSFLPS DFFPSIRDLL

301 DTASALYREA LESPEHCSPH HTALRQAILC WGELMNLATW VGSNLEDPAS RELVVSYVNV

361 NMGLKIRQLL WFHISCLTFG RETVLEYLVS FGVWIRTPPA ARPPNAPILS

TLPETTVV(HH

421 HHHH)
```

G28-8LH-HBcAg-His Protein
```
                                                       SEQ ID NO: 5
  1 METPAQLLFL LLLWLPDTTG DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSG GGGSGGGGSG GGGSGGGGSM DIDPYKEFGA

301 SVELLSFLPS DFFPSIRDLL DTASALYREA LESPEHCSPH HTALRQAILC WGELMNLATW

361 VGSNLEDPAS RELVVSYVNV NMGLKIRQLL WFHISCLTFG RETVLEYLVS FGVWIRTPPA

421 YRPPNAPILS TLPETTVV(HH HHHH)
```

1-20: Leader
Bold: G28-8VL
Underlined: Gyl-Ser linker
Bold and underlined: G28-8VH
Italicized and underlined: HBcAgY132A
C-terminus: 6xHis G28-8LH-HBcAg-His Mature Protein (leader sequence removed from SEQ ID NO: 5)
```
                                                       SEQ ID NO: 6
  1 DIQMTQSPAS LSASVGETVT ITCRASEKIY SYLAWYQQKQ GKSPQLLVYN AKTLAEGVPS

61 RFSVSGSGTQ FSLRINSLQP EDFGTYYCQH HFGSPRTFGG GTKLEIKDLG GGGSGGGGSG

121 GGGSGGGGST GEVQLQQSGP ELVKPGASMK ISCKASGYSF TGYTMNWVKQ SHGKTLEWIG

181 LINPYNGVTS YNQKFKDKAT LTVDKSSSTA YMELLSLTSE DSAIYYCARD YNYDYFDYWG

241 QGTTLTVSSG GGGSGGGGSG GGGSGGGGSM DIDPYKEFGA SVELLSFLPS DFFPSIRDLL

301 DTASALYREA LESPEHCSPH HTALRQAILC WGELMNLATW VGSNLEDPAS RELVVSYVNV

361 NMGLKIRQLL WFHISCLTFG RETVLEYLVS FGVWIRTPPA YRPPNAPILSTLPETTVV(HH

421 HHHH)
```

G28-8LH-HBcAgY132AFL-His Protein
```
                                                       SEQ ID NO: 8
  1 METPAQLLFL LLLWLPDTTG DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSG GGGSGGGGSG GGGSGGGGSM DIDPYKEFGA

301 SVELLSFLPS DFFPSIRDLL DTASALYREA LESPEHCSPH HTALRQAILC WGELMNLATW
```

361 <u>*VGSNLEDPAS RELVVSYVNV NMGLKIRQLL WFHISCLTFG RETVLEYLVS FGVWIRTPPA*</u>

421 <u>*ARPPNAPILS TLPETTVVRR RGRSPRRRTP SPRRRRSQSP RRRRSQSR*</u>(HH HHHH)

1-20: Leader
Bold: G28-8VL
Underlined: Gyl-Ser linker
Bold and underlined: G28-8VH
Italicized and underlined: Full length HBcAg protein with Y132A substitution
C-terminus: 6xHis G28-8LH-HBcAgY132AFL-His Mature Protein (leader sequence removed from SEQ ID NO: 8)

SEQ ID NO: 9

1 DIQMTQSPAS LSASVGETVT ITCRASEKIY SYLAWYQQKQ GKSPQLLVYN AKTLAEGVPS

61 RFSVSGSGTQ FSLRINSLQP EDFGTYYCQH HFGSPRTFGG GTKLEIKDLG GGGSGGGGSG

121 GGGSGGGGST GEVQLQQSGP ELVKPGASMK ISCKASGYSF TGYTMNWVKQ SHGKTLEWIG

181 LINPYNGVTS YNQKFKDKAT LTVDKSSSTA YMELLSLTSE DSAIYYCARD YNYDYFDYWG

241 QGTTLTVSSG GGGSGGGGSG GGGSGGGGSM DIDPYKEFGA SVELLSFLPS DFFPSIRDLL

301 DTASALYREA LESPEHCSPH HTALRQAILC WGELMNLATW VGSNLEDPAS RELVVSYVNV

361 NMGLKIRQLL WFHISCLTFG RETVLEYLVS FGVWIRTPPA ARPPNAPILS TLPETTVVRR

421 RGRSPRRRTP SPRRRRSQSP RRRRSQSR(HH HHHH)

G28-8LH-HBcAgFL-His Protein

SEQ ID NO: 11

1 METPAQLLFL LLLWLPDTTG DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG <u>GGGSGGGGSG GGGSGGGGST</u> <u>GEVQLQQSGP ELVKPGASMK ISCKASGYSF</u>

181 <u>TGYTMNWVKQ SHGKTLEWIG LINPYNGVTS YNQKFKDKAT LTVDKSSSTA YMELLSLTSE</u>

241 <u>DSAIYYCARD YNYDYFDYWG QGTTLTVSS</u>G <u>GGGSGGGGSG GGGSGGGGSM</u> <u>*DIDPYKEFGA*</u>

301 <u>*SVELLSFLPS DFFPSIRDLL DTASALYREA LESPEHCSPH HTALRQAILC WGELMNLATW*</u>

361 <u>*VGSNLEDPAS RELVVSYVNV NMGLKIRQLL WFHISCLTFG RETVLEYLVS FGVWIRTPPA*</u>

421 <u>*YRPPNAPILS TLPETTVVRR RGRSPRRRTP SPRRRRSQSP RRRRSQSR*</u>(HH HHHH)

1-20: Leader
Bold: G28-8VL
Underlined: Gyl-Ser linker
Bold and underlined: G28-8VH
Italicized and underlined: Full length HBcAg protein
C-terminus: 6xHis G28-8LH-HBcAgFL-His Mature Protein (leader sequence removed from SEQ ID NO: 11)

SEQ ID NO: 12

1 DIQMTQSPAS LSASVGETVT ITCRASEKIY SYLAWYQQKQ GKSPQLLVYN AKTLAEGVPS

61 RFSVSGSGTQ FSLRINSLQP EDFGTYYCQH HFGSPRTFGG GTKLEIKDLG GGGSGGGGSG

121 GGGSGGGGST GEVQLQQSGP ELVKPGASMK ISCKASGYSF TGYTMNWVKQ SHGKTLEWIG

181 LINPYNGVTS YNQKFKDKAT LTVDKSSSTA YMELLSLTSE DSAIYYCARD YNYDYFDYWG

241 QGTTLTVSSG GGGSGGGGSG GGGSGGGGSM DIDPYKEFGA SVELLSFLPS DFFPSIRDLL

301 DTASALYREA LESPEHCSPH HTALRQAILC WGELMNLATW VGSNLEDPAS RELVVSYVNV

361 NMGLKIRQLL WFHISCLTFG RETVLEYLVS FGVWIRTPPA YRPPNAPILS TLPETTVVRR

421 RGRSPRRRTP SPRRRRSQSP RRRRSQSR(HH HHHH)

G28-8scFVLH-HBeAg

SEQ ID NO: 18

METPAQLLFL LLLWLPDTTG DIQMTQSPAS LSASVGETVT ITCRASEKIY

SYLAWYQQKQ GKSPQLLVYN AKTLAEGVPS RFSVSGSGTQ FSLRINSLQP

EDFGTYYCQH HFGSPRTFGG GTKLEIKDLG GGGSGGGGSG GGGSGGGGST

GEVQLQQSGP ELVKPGASMK ISCKASGYSF TGYTMNWVKQ SHGKTLEWIG

LINPYNGVTS YNQKFKDKAT LTVDKSSSTA YMELLSLTSE DSAIYYCARD

YNYDYFDYWG QGTTLTVSSG GGGSGGGGSG GGGSGGGGSS *KLCLGWLWGM*

*DIDPYKEFGA SVELLSFLPS DFFPSIRDLL DTASALYREA LESPEHCSPH*

*HTALRQAILC WGELMNLATW VGSNLEDPAS RELVVSYVNV NMGLKIRQLL*

*WFHISCLTFG RETVLEYLVS FGVWIRTPPA YRPPNAPILS TLPETTVV*(HH

HHHH)

1-20: Leader
Bold: G28-8VL
Underlined: Gyl-Ser linkers
Bold and underlined: G28-8VH
Italicized and underlined: HBeAg
C-terminus: 6xHis Mature G28-8scFVLH-HBeAg protein (leader sequence removed from SEQ ID NO: 18)

SEQ ID NO: 19

DIQMTQSPAS LSASVGETVT ITCRASEKIY SYLAWYQQKQ GKSPQLLVYN

AKTLAEGVPS RFSVSGSGTQ FSLRINSLQP EDFGTYYCQH HFGSPRTFGG

GTKLEIKDLG GGGSGGGGSG GGGSGGGGST GEVQLQQSGP ELVKPGASMK

ISCKASGYSF TGYTMNWVKQ SHGKTLEWIG LINPYNGVTS YNQKFKDKAT

LTVDKSSSTA YMELLSLTSE DSAIYYCARD YNYDYFDYWG QGTTLTVSSG

GGGSGGGGSG GGGSGGGGSS KLCLGWLWGM DIDPYKEFGA SVELLSFLPS

DFFPSIRDLL DTASALYREA LESPEHCSPH HTALRQAILC WGELMNLATW

VGSNLEDPAS RELVVSYVNV NMGLKIRQLL WFHISCLTFG RETVLEYLVS

FGVWIRTPPA YRPPNAPILS TLPETTVV(HH HHHH)

HBeAg-G28-8scFVLH

SEQ ID NO: 20

MQLFPLCLII SCSCPTVQAS *KLCLGWLWGM DIDPYKEFGA SVELLSFLPS*

*DFFPSIRDLL DTASALYREA LESPEHCSPH HTALRQAILC WGELPMLATW*

*VGSNLEDPAS RELVVSYVNV NHGLKIRQLL WFHISCLTFG RETVLEYLVS*

*FGVWIRTPPA YRPPNAPILS TLPETTVV*GG GGSGGGGSGG GGSGGGGSDI

QMTQSPASLS ASVGETVTIT CRASEKIYSY LAWYQQKQGK SPQLLVYNAK

TLAEGVPSRF SVSGSGTQFS LRINSLQPED FGTYYCQHHF GSPRTFGGGT

KLEIKDLGGG GSGGGGSGGG GSGGGGSTGE VQLQQSGPEL VKPGASMKIS

CKASGYSFTG YTMNWVKQSH GKTLEWIGLI NPYNGVTSYN QKFKDKATLT

-continued

VDKSSSTAYM ELLSLTSEDS AIYYCARDYN YDYFDYWGQG TTLTVSS(HHH

HHH)

1-19: Leader
Bold: G28-8VL
Underlined: Gyl-Ser linkers
Bold and underlined: G28-8VH
Italicized and underlined: HBeAg
C-terminus: 6xHis Mature HBeAg-G28-8scFVLH protein

SEQ ID NO: 21

SKLCLGWLWG MDIDPYKEFG ASVELLSFLP SDFFPSIRDL LDTASALYRE

ALESPEHCSP HHTALRQAIL CWGELMNLAT WVGSNLEDPA SRELVVSYVN

VNMGLKIRQL LWFHISCLTF GRETVLEYLV SFGVWIRTPP AYRPPNAPIL

STLPETTVVG GGGSGGGSG GGGSGGGSD IQMTQSPASL SASVGETVTI

TCRASEKIYS YLAWYQQKQG KSPQLLVYNA KTLAEGVPSR FSVSGSGTQF

SLRINSLQPE DFGTYYCQHH FGSPRTFGGG TKLEIKDLGG GGSGGGGSGG

GGSGGGGSTG EVQLQQSGPE LVKPGASMKI SCKASGYSFT GYTMNWVKQS

HGKTLEWIGL INPYNGVTSY NQKFKDKATL TVDKSSSTAY MELLSLTSED

SAIYYCARDY NYDYFDYWGQ GTTLTVSS(HH HHHH)

Purple: Leader
Brown: G28-8VL
Red: Gyl-Ser linker
Black: G28-8VH
Blue: Full length HBeAg protein
Bright green: 6xHis The compositions of any embodiment or combination of embodiments of the invention may be provided as a stand-alone composition, or may be provided as part of a molecular scaffold. In various embodiments, the composition may be attached to molecular scaffold. Any suitable scaffold can be used, including but not limited to a VNAR single domain antibody (shark variable new antigen receptor), a lamprey variable lymphocyte receptor, a Im 7 (colicin immunity 7 protein), an anticalin (lipocalin transport proteins), an FN3 (fibronectin 3) monobody, a DARPin (designed ankyrin repeat proteins), an affibody (Z domain of protein A), etc., with CD180-binding polypeptide loops.

In another embodiment, the composition of any embodiment or combination of embodiments of the invention further comprises an adjuvant. While adjuvant is not required to induce rapid activation of HBcAg and/or HBeAg-specific B cells, addition of adjuvant to the compositions can result in additional enhancement of the immune response when the compositions are used in the methods of the invention. Any suitable adjuvant can be used, including but not limited to inorganic compounds (aluminum hydroxide, aluminum phosphate, calcium phosphate hydroxide, beryllium, etc.), mineral oil, detergents, cytokines, toll-like receptor agonists, Freund's complete adjuvant, Freund's incomplete adjuvant, squalene, etc. In a preferred embodiment, the adjuvant comprises or consists of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion. The adjuvant may be present in the composition as an unlinked component or a linked component, depending on the adjuvant used.

In another embodiment, the compositions of the invention can be modified to extend half-life, such as by attaching at least one molecule to the composition for extending serum half-life, including but not limited to a polyethlyene glycol (PEG) group, serum albumin, transferrin, transferrin receptor or the transferrin-binding portion thereof, or combinations thereof. As used herein, the word "attached" refers to a covalently or noncovalently conjugated substance. The conjugation may be by genetic engineering or by chemical means.

The compositions of the present invention may be stored in any suitable buffer.

In a second aspect, the present invention provides isolated nucleic acids encoding the composition of any embodiment of the first aspect of the invention. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In various non-limiting embodiments, the isolated nucleic acids encode the polypeptide of any one of SEQ ID NOS: 2, 3, 5, 6, 8, 9, 11, or 12. In other embodiments, the isolated nucleic acids comprise or consist of the nucleotide sequence of SEQ ID NO:1, 4, 7, or 10.

In a third aspect, the present invention provides nucleic acid vectors comprising the isolated nucleic acid of the second aspect of the invention. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

The nucleic acids and vectors of the invention can be used not only for production of large quantities of the compositions of the invention, but also for use as a nucleic acid (such as a DNA) vaccine administered by gene gun or other methods.

In a fourth aspect, the present invention provides recombinant host cells comprising the nucleic acid vector of the third aspect of the invention. The host cells can be either prokaryotic or eukaryotic. The cells can be transiently or stably transfected. Such transfection of expression vectors into prokaryotic and eukaryotic cells (including but not limited to Chinese hamster ovary (CHO) cells) can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.).

The recombinant host cells can be used, for example in methods for producing antibody (when the binding protein is an antibody), comprising:

(a) culturing the recombinant host cell of the invention under conditions suitable for expression of the nucleic-acid encoded antibody composition; and (b) isolating the antibody composition from the cultured cells.

Suitable conditions for expression of the nucleic-acid encoded antibody composition can be determined by those of skill in the art based on the teachings herein, the specific host cells and vectors used, and the general knowledge of those of skill in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein.

In a fifth aspect, the present invention provides pharmaceutical compositions, comprising:

(a) the composition, isolated nucleic acid, or recombinant expression vector of any embodiment or combination of embodiments disclosed herein; and (b) a pharmaceutically acceptable carrier.

In this embodiment, the compositions of the invention are present in a pharmaceutical formulation. In this embodiment, the compositions are combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical composition may comprise in addition to the composition of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions of the invention may be made up in any suitable formulation, preferably in formulations suitable for administration by injection. Such pharmaceutical compositions can be used, for example, in methods of use as vaccines, prophylactics, or therapeutics.

The pharmaceutical compositions may contain any other components as deemed appropriate for a given use, such as additional therapeutics or vaccine components. In one embodiment, the pharmaceutical compositions further comprise toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

In a sixth aspect, the present invention provides methods for treating or limiting development of an HBV infection or a hepatitis-B virus (HBV)-related disorder, comprising administering to an individual in need thereof an amount effective to treat or limit development of the disorder of the composition, isolated nucleic acid, recombinant expression vector, or pharmaceutical composition, or a pharmaceutical salt thereof, of any embodiment or combination of embodiments of the present invention. In one embodiment, the compositions are used prophylactically as vaccines to limit development of HBV infection disease/severity of infectious disease, such as in individuals that have not been exposed to an infectious agent but are at risk of such exposure. In other embodiments, the methods can be used therapeutically to treat people exposed to or chronically infected with HBV.

The methods of the invention target antigen to CD180, a surface protein expressed on B cells, macrophages, and dendritic cells, that to produce antigen-specific IgG in the absence of T cell costimulation (such as CD40 deficiency) or the complete absence of T cells (such as TCR β/δ deficiency). Thus, the methods can be used in any therapeutic or prophylactic treatment for HBV infection or vaccination. This approach also finds use, for example, for neonates, the elderly, and the immunodeficient, both in specifically targeting cellular populations enriched in underdeveloped or otherwise deficient immune systems and by improving responses to antigens that require linked recognition (carbohydrate epitopes, etc.).

As used herein, "treat" or "treating" means accomplishing one or more of the following in an individual that already has a disorder or has already been exposed to a disorder-causing substance/pathogen: (a) reducing the severity of the disorder; (b) limiting or preventing development of symptoms characteristic of the disorder(s) being treated (ex: immune deficiencies in cancer patients or other patients) undergoing chemotherapy and/or radiation therapy); (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "limiting" or "limiting development of" means accomplishing one or more of the following in an individual that does not have the disorder to be limited: (a) preventing the disorder; (b) reducing the severity of the disorder; and (c) limiting or preventing development of symptoms characteristic of the disorder.

As used herein, an "amount effective" refers to an amount of the composition that is effective for treating and/or limiting the relevant disorder.

While the methods of the invention do not require use of an adjuvant, the methods may further comprise administering an adjuvant for possible additional enhancement of the immune response Any suitable adjuvant can be used, including but not limited to toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

The individual may be any suitable individual, including but not limited to mammals. Preferably the individual is a human. In one embodiment, the individual has a T-cell deficiency and/or a defect in co-stimulation between B cells and T cells, or is immuno-compromised by chronic infections or from acute or chronic taking of immunosuppressive drugs for treatment of autoimmune diseases, or other inflammatory disease. In another embodiment, the individual is less than one month old or is elderly (i.e.: at least 65 years old).

In various other embodiments, the individual has a hepatitis B-related disease, such as hepatitis, hepatitis-related disease, fulminant hepatitis, cirrhosis, and/or hepatocellular carcinoma, and the methods are used to treat the a hepatitis B-related disease, such as hepatitis, hepatitis-related disease, fulminant hepatitis, cirrhosis, and/or hepatocellular carcinoma.

Example 1

Generation and Characterization of G28-8LH-HBcAgY13A-his Recombinant Vaccine Molecule g28-8 (Anti-Human Cd180) scFv-HBcAg Recombinant Vaccine Molecules.

The inventors have demonstrated that for the specific anti-CD180 antibody, G28-8, a single chain antibody (scAb) in the form of VLVH-human IgG1 Fc retains both the efficient binding as well as the biological properties of its parent G28-8 IgG. The G28-8LH single chain Fv (scFv) was used to create G28-8scFv-HBcAg recombinant vaccine constructs. scFv generated from other anti-CD180 antibodies should retain the antibody characteristics in either the VLVH, or the VHVL configuration.

HBV Capsid Proteins that do not Self-Assemble can be Attached to Anti-CD180 scFv and Expressed.

Normally HBV capsid proteins (HBcAgs) self-assemble around the pre-genomic HBV RNA and the viral reverse transcriptase. The assembly domain of the HBcAg plays a key role in the assembly of the capsid and its stability. The tyrosine residue Y132 is required to stabilize the interactions between HBV core Ag dimers, which in turn is required for icosahedral capsids to form. HBcAg proteins with a single mutation at Y132 to alanine (Y132A) have defective capsid assembly.[38,39] The HBcAgY132A mutant is a stable dimer but unlike wildtype HBcAg, does not assemble into capsids even at high salt solution (1 M NaCl). Because HBcAg-Y132A proteins form dimers and crosslinking of CD180 is required for optimal signaling, we proposed that anti-CD180 scFv-HBcAgY132A proteins may form dimers. Because scFv G28-8LH has shown to retain the binding and B cell stimulatory activity, it was used to construct the recombinant vaccine molecule consisting of HBcAgY132A. The dimeric nature of anti-CD180 scFv in such G28-8LH-HBcAgY132A protein was in turn be able to functionally engage CD180 molecules on antigen-presenting to activate them, e.g., activation of B cells. We designed a DNA sequence encoding a protein comprised of the VL and VH domains of G28-8 (anti-CD180), a Glycine-Serine linker, the HBcAgY132A mutant protein, and a His tag at the C-terminal for affinity purification of the recombinant vaccine molecule (FIG. 1, SEQ ID NO:1).

```
G28-8LH-HBcAgY132A-His
                                                           SEQ ID NO: 1
    1 GCGAAGCTTT GAGCCACCAT GGAAACCCCA GCGCAGCTTC TCTTCCTCCT GCTACTCTGG

61 CTCCCAGATA CCACCGGTGA CATCCAGATG ACTCAGTCTC CAGCCTCCCT ATCTGCATCT

121 GTGGGAGAAA CTGTCACCAT CACATGTCGA GCAAGTGAGA AGATTTACAG TTATTTAGCA

181 TGGTATCAGC AGAAACAGGG AAAATCTCCT CAGCTCCTGG TCTATAACGC AAAAACCTTA

241 GCAGAAGGTG TGCCATCAAG GTTCAGTGTC AGTGGATCAG GCACACAGTT TTCTCTGAGG

301 ATCAACAGCC TGCAGCCTGA AGATTTTGGG ACTTATTACT GTCAACATCA TTTTGGTTCT

361 CCTCGGACGT TCGGTGGAGG CACCAAACTG GAAATCAAAG ATCTCGGAGG AGGTGGCTCA

421 GGTGGTGGAG GATCTGGAGG AGGTGGGAGT GGTGGAGGTG GTTCTACCGG TGAGGTCCAG

481 CTGCAACAGT CTGGACCTGA ACTGGTGAAG CCTGGAGCTT CAATGAAGAT ATCCTGCAAG

541 GCTTCTGGTT ACTCATTCAC TGGCTACACC ATGAACTGGG TGAAGCAGAG CCATGGAAAG

601 ACCCTTGAAT GGATTGGACT TATTAATCCT TACAATGGTG TTACTAGCTA CAACCAGAAG

661 TTCAAGGACA AGGCCACATT AACTGTAGAC AAGTCATCCA GCACAGCCTA CATGGAACTC

721 CTCAGTCTGA CATCTGAGGA CTCTGCAATC TATTACTGTG CAAGAGACTA TAATTACGAC

781 TACTTTGACT ACTGGGGCCA AGGCACCACT CTCACAGTCT CCTCAGGAGG AGGTGGCTCA

841 GGTGGTGGAG GATCTGGAGG AGGTGGGAGT GGTGGAGGTG GTTCTATGGA CATTGACCCG

901 TATAAAGAAT TTGGAGCTTC TGTGGAGTTA CTCTCTTTTT TGCCTTCTGA CTTCTTTCCT

961 TCTATTCGAG ATCTCCTCGA CACCGCCTCT GCTCTGTATC GGGAGGCCTT AGAGTCTCCG

1021 GAACATTGTT CACCTCACCA TACAGCACTC AGGCAAGCTA TTCTGTGTTG GGGTGAGTTG

1081 ATGAATCTGG CCACCTGGGT GGGAAGTAAT TTGGAAGACC CAGCATCCAG GGAATTAGTA

1141 GTCAGCTATG TCAATGTTAA TATGGGCCTA AAAATTAGAC AACTATTGTG GTTTCACATT

1201 TCCTGCCTTA CTTTTGGAAG AGAAACTGTC CTTGAGTATT TGGTGTCTTT TGGAGTGTGG

1261 ATTCGCACTC CTCCCGCTGC CAGACCACCA AATGCCCCTA TCTTATCAAC ACTTCCGGAA

1321 ACTACTGTTG TTCACCACCA TCATCATCAT TGATAAGGAT CCGCG

5' end HindIII and 3' end BamHI sites for directional cloning into
appropriate expression vector
Kozak consensus, GCCACC, right before 5' ATG start codon
One 5' in frame stop codon after 5' end HindIII site
Two in frame stop codons before 3' end BamHI site
```

The native leader sequence from the VL domain of G28-8 was included to facilitate secretion of the recombinant vaccine molecules from the host CHO cells (SEQ ID NO: 1, SEQ ID NO:2).

```
G28-8LH-HBcAgY132A-His Protein
                                                           SEQ ID NO: 2
    1 METPAQLLFL LLLWLPDTTG DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSG GGGSGGGGSG GGGSGGGGSM DIDPYKEFGA
```

-continued

```
301 SVELLSFLPS DFFPSIRDLL DTASALYREA LESPEHCSPH HTALRQAILC WGELMNLATW

361 VGSNLEDPAS RELVVSYVNV NMGLKIRQLL WFHISCLTFG RETVLEYLVS FGVWIRTPPA

421 ARPPNAPILS TLPETTVV(HH HHHH)

1-20: Leader
Bold: G28-8VL
Underlined: Gyl-Ser linkers
Bold and underlined: G28-8VH
Italicized and underlined: HBcAgY132A
C-terminus: 6xHis
```

The predicted mature polypeptide sequence after the cleavage of the leader sequence is given in SEQ ID NO: 3. The HBcAgY132A sequence in this vaccine construct consists of amino acid residues 1 to 149 of HBcAg without the C-terminal arginine-rich 50 resides of 150-183.

```
G28-8LH-HBcAgY132A-His Mature Protein (leader sequence removed
from SEQ ID NO: 2)
                                                           SEQ ID NO: 3
  1 DIQMTQSPAS LSASVGETVT ITCRASEKIY SYLAWYQQKQ GKSPQLLVYN AKTLAEGVPS

61 RFSVSGSGTQ FSLRINSLQP EDFGTYYCQH HFGSPRTFGG GTKLEIKDL G

GGGSGGGGSG

121 GGGSGGGGST GEVQLQQSGP ELVKPGASMK ISCKASGYSF TGYTMNWVKQ SHGKTLEWIG

181 LINPYNGVTS YNQKFKDKAT LTVDKSSSTA YMELLSLTSE DSAIYYCARD YNYDYFDYWG

241 QGTTLTVSSG GGGSGGGGSG GGGSGGGGSM DIDPYKEFGA SVELLSFLPS DFFPSIRDLL

301 DTASALYREA LESPEHCSPH HTALRQAILC WGELMNLATW VGSNLEDPAS RELVVSYVNV

361 NMGLKIRQLL WFHISCLTFG RETVLEYLVS FGVWIRTPPA ARPPNAPILS

TLPETTVV(HH

421 HHHH)
```

Production of Recombinant the G28-8LH-HBcAgY132A-his Protein.

Complementary DNAs (cDNAs) encoding the G28-8LH-HBcAgY132A-His recombinant proteins (FIG. 1, SEQ ID NO:1) were cloned into the mammalian expression vector pTT5 that harbors a CMV promoter to drive protein expression. Transient transfection of these plasmids into Chinese hamster ovary (CHO) cells was done using Lipofectamine reagents (Invitrogen Carlsbad, Calif.) or polyethyleninmine (PEI). Small-scale transfection optimization using 5%, 20% and 80% ratios of expression plasmid in the lipofection reagent was conducted to identify to optimal plasmid to lipofection reagent ratios for larger scale expression. Nickel affinity chromatography, e.g., using the HisPurNi-NTA resin (Thermo Fisher Scientific Inc., Rockford Ill.), was used to purify the recombinant proteins. The cDNA sequences for the G28-8LH-HBcAgY132A-His protein predicts a polypeptide size of ~45 kDa.

FIG. 2 shows the results from a 2-liter expression run. The plasmid encoding the G28-8LH-HBcAg-Y132A-His protein was transiently expressed in CHO cells for 8 days. Culture supernatants (~2 liters) were collected and cellular debris was removed by centrifugation. Clarified culture supernatants were then loaded on to a column containing HisPurNi-NTA resin. After washing the column with the wash buffer (50 mM phosphate buffer, pH 7.0, 300 mM NaCl, 1 mM imidazole), bound recombinant protein was eluted with the elution buffer (50 mM phosphate buffer, pH 7.0, 300 mM NaCl, 150 mM imidazole). Protein containing fractions as monitored by absorbance at 280 nM were collected, pooled, and dialyzed against phosphate-buffer saline at pH 7.0. Purified G28-8LH-HBcAgY312A-His and unbound flow through materials from HisPurNi-NTA chromatography was analyzed on SDS-PAGE (4-15% gradient under reducing conditions) stained with Coomassie blue. FIG. 2, left panel shows a major protein band migrating at the predicted MW of ~45 kDa, suggesting that G28-8LH-HBcAgY132A-His protein was in fact expressed by CHO cells as an intact protein and secreted into the culture supernatants. A duplicate gel was then transferred onto a nylon membrane and immuno-blotted with an anti-6x-His antibody. Intense anti-6xHis signals were only observed at ~45 kDa (FIG. 2, right panel), at the identical MW G28-8LH-HBcAgY132A-His migrated to on the Coomassie blue stained gel (FIG. 2, left panel).

Example 2

Characterization of G28-8LH-HBcAgY132A-his

Figure 3:
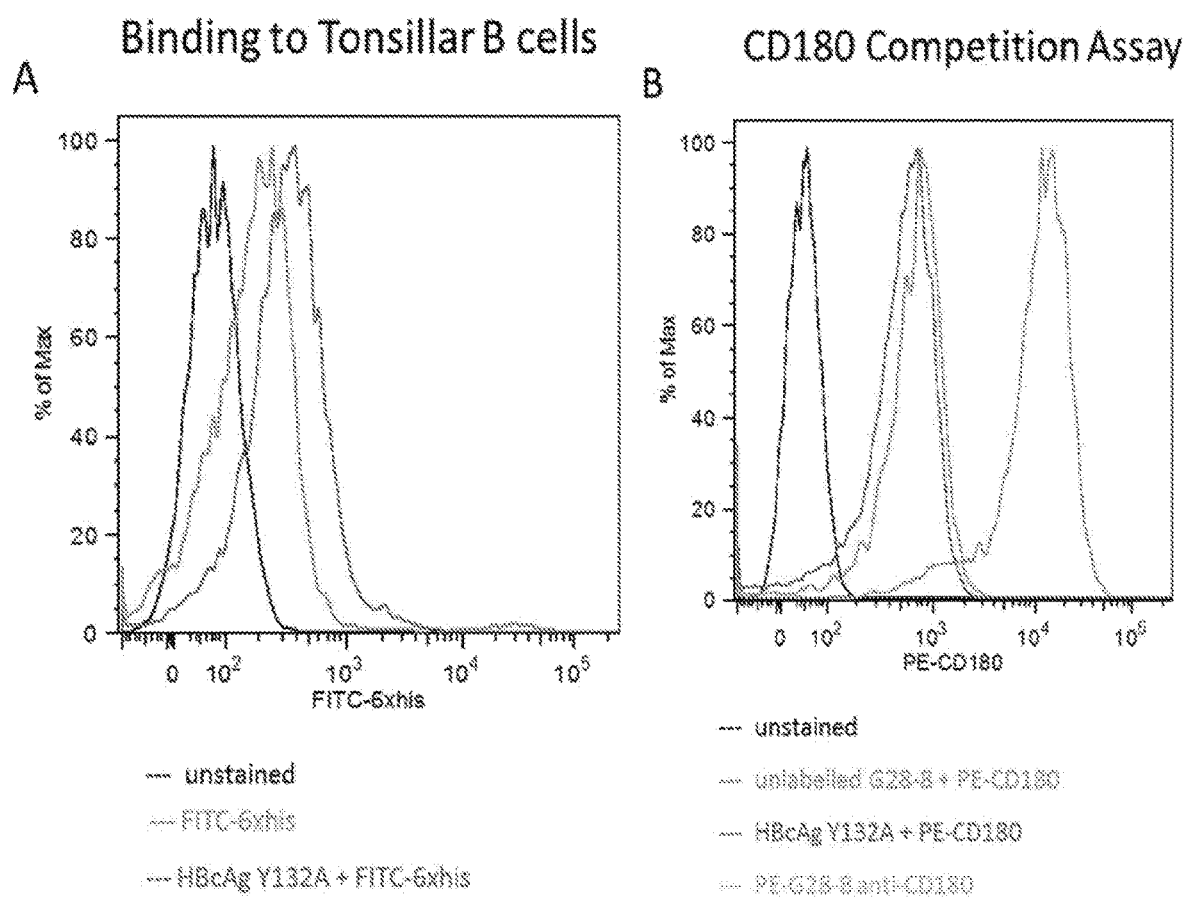

FIG. 3A shows that human CD20+ tonsillar B cells ($10^6$) were incubated in 96 well round bottom plates with PBSA (PBS w/0.2% BSA+0.2% NaN3) media only (green) or with PBSA with the following His tagged recombinant protein containing the light and heavy chains of G28-8 anti-human CD180 (LH) and G28-8LH-HBcAgY132A-His (blue), at 10 μg/ml. After a 40 min incubation on ice, the cells were washed twice (centrifuged at 1200 rpm, 4 min). Then 100 μl of PBSA+5 μl a fluorescein (FITC)-conjugated anti 6xHis (FITC-6x-His epitope tag ThermoScientific MA1-81891) were added to the wells, and after a 40 min incubation on ice, cells were washed twice and the level of fluorescence measured by flow cytometry shown on abscissa (log scale). Unstained cells shown in black. The recombinant protein bound to B cells as shown by binding being above the FITC control, demonstrating binding to CD180 expressed on B cells.

As a second test for binding, a competition assay was performed (FIG. 3B). For negative and positive controls human B cells were either unstained (black) or stained with R-phycoerytherin G28-8 anti-CD180 (G28-8-PE, purple), respectively. Other tubes of B cells were first treated with 2.5 µg of either G28-8 mAb (green) or LH-HBcAgY132A-His (blue), for 40 min on ice, after which 10 µg G28-8-PE was added. After an incubation of 40 min on ice, cells were washed twice and analyzed by flow cytometry. As expected G28-8 mAb blocked the binding of G28-8-PE and reduced the level of fluorescence detected (green). G28-8LH-HBcAgY132A-His (blue) was as effective as the native G28-8 mAb at blocking binding, demonstrating that it bound effectively to human B cells and recognized CD180 specifically.

Figure 4:
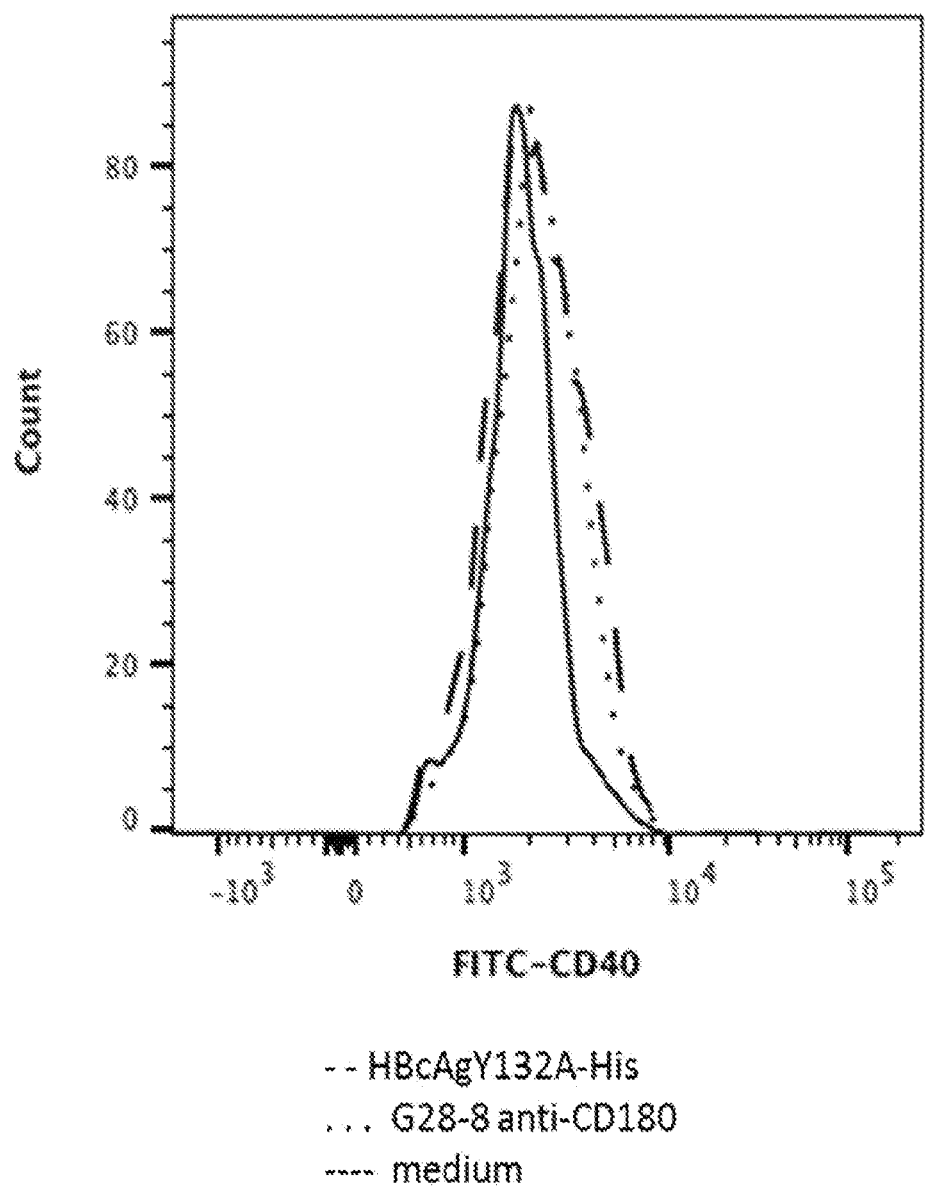

The ability of G28-8LH-HBcAgY132A-His to upregulate CD40 expression was then tested to evaluate its functional activity. Er-blood mononuclear cells enriched for B cells were incubated for 24 hrs at 37° C. with either media (black line) or 10 µg/ml of G28-8 (dotted line) or 10 µg/ml G28-8LH-HBcAgY132A-His. Samples were washed twice with PBSA, stained with mAb specific for CD20 (Pacific Blue Biolegend) and CD40 (FITC BD BioSciences) and evaluated for CD40 and CD20 expression using flow cytometry. FIG. 4 shows CD40 expression of gated CD20$^+$ B cells. Both G28-8 and G28-8LH-HBcAgY132A-His upregulated CD40 expression to a similar extent, confirming that G28-8LH-HBcAgY132A-His was functionally active.

Example 3

Induction by G28-8LH-HBcAgY132A-his Vaccine of HBcAg-Specific IgG Antibody Responses in Rhesus Macaques The ability of G28-8LH-HBcAg132A-His to induce humoral and cellular immune responses was examined in a vaccination experiment in rhesus macaques (*Macaca mulatta*). Groups of rhesus macaques (N=3) were vaccinated subcutaneously with either: 1) 300 µg of G28-8LH-HBcAgY132A-His (αCD180-HBVAg) in 1 ml; 2) 300 µg of G28-8LH-HBcAgY132A-His (HBcAg-CD180) plus 1 mg of long chain poly I:C (InvivoGen, San Diego) in 1 ml; 300 μg of G28-8LH-HBcAgY132A-His (HBcAg-CD180) plus 1 mg CpGB (Coley Pharmaceuticals) in 1 ml; or 4) 16 micrograms of G28-8LH-HBcAgY132A-His encoding plasmid DNA (HBcAg-CD180 DNA) coated onto 1 micron gold beads at a rate of 2.0 μg DNA per mg gold particles. The particles were then injected intracellularly into the epidermis of the skin using a gene gun (GG) as described.[41] Animals were vaccinated on days 0, 30 and 81, and on days 0, 7, 14, 30 (time-points after first dose), 44, 62, 76, 90 (time-points after second dose), 111, 118, 125, 139 and 164 (time-points after 3rd dose), serum and heparinized blood samples were obtained. Serum samples were assessed for IgG antibody responses to HBcAg by ELISA as follows: a) coating 96 well plates with 200 ng/well recombinant HBcAg (expressed in yeast); b) adding serial dilutions of serum samples (100 μl diluted in TBS+0.05% tween-20) starting with a 1:1000 dilution, followed by washing and adding HRP-anti-macaque IgG second step (Rockland, 1:5000 dilution). All four groups produced IgG after immunizations (FIG. 5). The antibody titers increased after each boost. The group receiving vaccine with a CpGB adjuvant had significantly higher IgG antibody responses compared to the other three groups.

Example 4

Induction of HBcAg-Specific CD4 and CD8 T Cell Responses by G28-8LH-HBcAgY132A-His in Rhesus Macaques To determine the frequency of HBcAg-specific, intracellular cytokine-producing CD4 and CD8 T cells after vaccination of macaques, peripheral blood mononuclear cells were isolated from heparinized blood samples obtained from immunized macaques 28 days after the final dose on day 81 as noted in Example 3 and resuspended in growth media at defined concentrations (~1.2 million cells/condition). Cells were plated together with either: Staphylococcal enterotoxin B (SEB, Toxin Technology, Sarasota) or PMA/lonomycin (positive controls); HBcAg peptide pools (Table 1, experimental); or DMSO (neg control) at the same concentration as in the peptide pools. After an incubation for 1 hr at 37° C. to initiate stimulation, brefeldin A was added to retain cytokines in the cells. Cells were then incubated for an additional 11-14 hrs, after which staining was initiated. First, cells were stained to detect surface markers: CD3, CD4, CD8 and CD107 (a marker of cytolytic effector function), then cells were fixed, permeabilized and stained with antibodies that detect intracellular cytokines (IFNγ, TNFα or IL-2). Cells were then analyzed using an LSRII flow cytometer. Analyses were performed using PBMCs obtained 28 days after a second booster vaccination first treated as follows: Cells ($1.2\times10^6$) were stimulated in 96 well plates with 37 HBcAg peptides (Table 1) divided into 2 pools of n=18 and n=19 peptides at 2 μg/ml together with costimulatory anti-CD28 and anti-CD49d antibodies (5 μg/ml in total volume of 200 μl) for 1 hour at 37 C. Cells in control wells were incubated with medium only (negative control) or with SEB enterotoxin (5 μg/ml, positive control). Brefeldin A (Sigma) was added to wells at a final concentration of 0.05 μg/ml, and then cells were incubated for an additional 5 hours at 37 C, after which plates were wrapped in plastic and aluminum foil and incubated overnight at 4 C. Cells were then centrifuged and washed with PBS and stained with a live/dead cell stain (Invitrogen), incubated for 10 minutes (min) at room temperature (RT), washed and then stained with sets of chromophore-labeled monoclonal antibodies (mAbs) specific for cell surface markers included CD3-APC, CD4-PerCP Cy5.5, CD8-APC-Cy7, CD28-PECF594 and CD107a/b-FITC (all Becton Dickinson, BD) and CCR7-PerCPefluor710 (eBioscience) at 1:50 dilution, 50 μl. After a 30 min incubation in the dark at RT, cells were centrifuged and washed with PBS and then treated with BD Fixation/Permeabilization Solution (1×, BD #554714), incubated in the dark for 20 min at RT, and washed twice with 200 μl/well of wash buffer. After removal of this wash buffer, cells were stained with 100 μl of a combination of TNFα-PE Cy7 1:20 (BD), IL-2 PE 1:10 (Biolegend) or IFNγ-V450 1:20 (Biolegend), mixed, and incubated for 60 min at 4 C. Cells were then washed with buffer and fixed with 2% paraformaldehyde in PBS for at least 1 hour at 4 C before analysis using an LSR II flow cytometer. FIG. 6 shows the net percent of CD3+ CD4+ cells (black) or CD3+CD8+ cells (gray) that expressed IFNγ, TNFα, IL-2 or CD107 for each vaccinated group after background levels (percent frequencies measured in unstimulated DMSO groups) are subtracted. Vaccination with the G28-8LH-HBcAgY132A-His protein only induced clear CD4 and CD8 T cell responses including IFNγ+ and CD107+ CD8+ T cell responses that are known to contribute to cytotoxic T cell activity.

TABLE 1

| Peptide number | NH2 terminal (left) |
|---|---|
| 1 (SEQ ID NO: 26) | SKLCLGWLWGMDIDP |
| 2 (SEQ ID NO: 27) | LGWLWGMDIDPYKEF |
| 3 (SEQ ID NO: 28) | WGMDIDPYKEFGASV |
| 4 (SEQ ID NO: 29) | IDPYKEFGASVELLS |
| 5 (SEQ ID NO: 30) | KEFGASVELLSFLPS |
| 6 (SEQ ID NO: 31) | ASVELLSFLPSDFFP |
| 7 (SEQ ID NO: 32) | LLSFLPSDFFPSIRD |
| 8 (SEQ ID NO: 33) | LPSDFFPSIRDLLDT |
| 9 (SEQ ID NO: 34) | FFPSIRDLLDTASAL |
| 10 (SEQ ID NO: 35) | IRDLLDTASALYREA |
| 11 (SEQ ID NO: 36) | LDTASALYREALESP |
| 12 (SEQ ID NO: 37) | SALYREALESPEHCS |
| 13 (SEQ ID NO: 38) | REALESPEHCSPHHT |
| 14 (SEQ ID NO: 39) | ESPEHCSPHHTALRQ |
| 15 (SEQ ID NO: 40) | HCSPHHTALRQAILC |
| 16 (SEQ ID NO: 41) | HHTALRQAILCWGEL |
| 17 (SEQ ID NO: 42) | LRQAILCWGELMNLA |
| 18 (SEQ ID NO: 43) | ILCWGELMNLATWVG |
| 19 (SEQ ID NO: 44) | GELMNLATWVGSNLE |
| 20 (SEQ ID NO: 45) | NLATWVGSNLEDPAS |
| 21 (SEQ ID NO: 46) | WVGSNLEDPASRELV |
| 22 (SEQ ID NO: 47) | NLEDPASRELVVSYV |
| 23 (SEQ ID NO: 48) | PASRELVVSYVNVNM |
| 24 (SEQ ID NO: 49) | ELVVSYVNVNMGLKI |
| 25 (SEQ ID NO: 50) | SYVNVNMGLKIRQLL |
| 26 (SEQ ID NO: 51) | VNMGLKIRQLLWFHI |
| 27 (SEQ ID NO: 52) | LKIRQLLWFHISCLT |
| 28 (SEQ ID NO: 53) | QLLWFHISCLTFGRE |
| 29 (SEQ ID NO: 54) | FHISCLTFGRETVLE |
| 30 (SEQ ID NO: 55) | CLTFGRETVLEYLVS |
| 31 (SEQ ID NO: 56) | GRETVLEYLVSFGVW |
| 32 (SEQ ID NO: 57) | VLEYLVSFGVWIRTP |
| 33 (SEQ ID NO: 58) | LVSFGVWIRTPPAYR |
| 34 (SEQ ID NO: 59) | GVWIRTPPAYRPPNA |
| 35 (SEQ ID NO: 60) | RTPPAYRPPNAPILS |

TABLE 1-continued

| Peptide number | NH2 terminal (left) |
|---|---|
| 36 (SEQ ID NO: 61) | AYRPPNAPILSTLPE |
| 37 (SEQ ID NO: 62) | PNAPILSTLPETTVV |

Example 5

Figure 7:
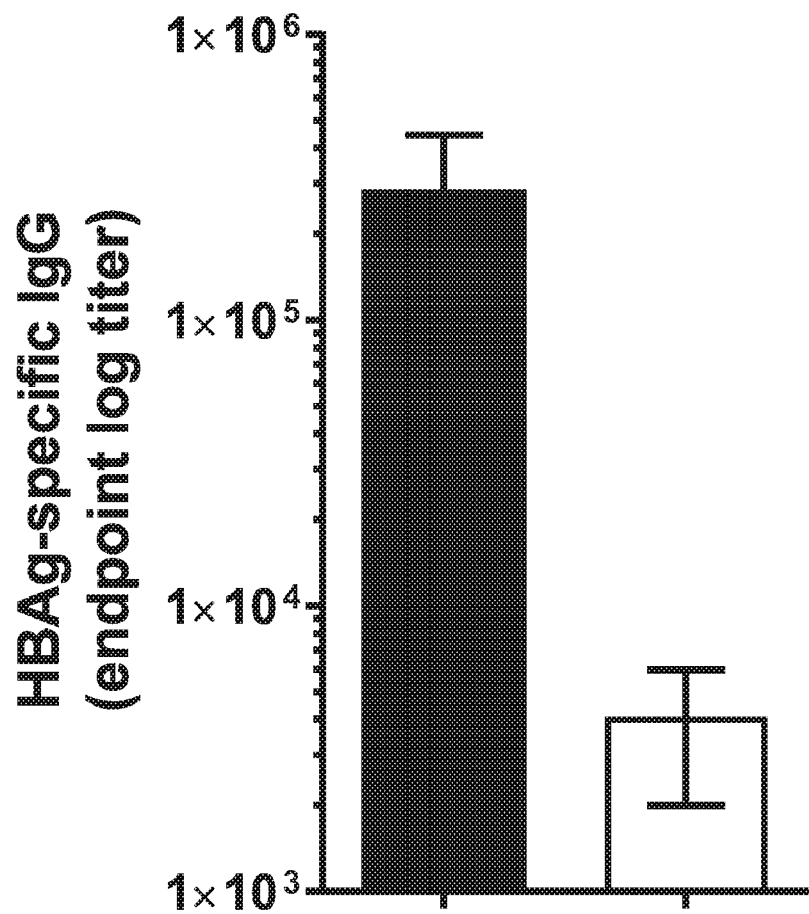

Induction of HBcAg-Specific IgG Antibody Responses in Rhesus Macaques by G28-8LH-HBcAgY132A-His Vaccine but not by HBcAgY132A-His Only Whether or not targeted of HBcAg132A-His to CD180 was required to induce a humoral immune response was examined in a vaccination experiment in rhesus macaques (*Macaca mulatta*). Two groups of rhesus macaques (N=3) were vaccinated subcutaneously with either: 1) 300 μg of G28-8LH-HBcAgY132A-His (αCD180-HBVAg) in 1 ml; or 2) 150 μg of HBcAgY132A-His, which was equivalent to the amount of HBcAgY132A-His used in Group 1 where it was attached to G28-8LH. Animals were vaccinated on days 0 and 30 and on days 0 (prebleed) and 44 (14 days after second dose) serum and heparinized blood samples were obtained. Serum samples were assessed for IgG antibody responses to HBcAgY132A by ELISA as follows: a) coating 96 well plates with 200 ng/well recombinant HBcAgY132A (expressed in CHO cells as in FIG. 2); b) adding serial dilutions of serum samples (100 μl diluted in TBS+0.05% tween-20) starting with a 1:1000 dilution, followed by washing and adding HRP-anti-macaque IgG second step (Rockland, 1:5000 dilution). Only macaques in Group 1 produced IgG after immunizations (FIG. 7). The antibody titers in Group 2 were similar to titers in prebleed serum samples (not shown). Thus, targeting to CD180 via G28-8LH-HBcAgY132A-His is required to induce strong HBcAg-specific IgG antibody responses.

LITERATURE CITED

1. DiMattia M A, Watts N R, Stahl S J, Grimes J M, Steven A C, Stuart D I, Wingfield P T. Antigenic switching of hepatitis B virus by alternative dimerization of the capsid protein. Structure. 2013. 21:133-42.
2. Kim H. N., et al., Hepatitis B vaccination in HIV-infected adults: current evidence, recommendations and practical considerations. International journal of STD & AIDS, 2009. 20:595-600.
3. Kubba, A. K., et al., Non-responders to hepatitis B vaccination: a review. Communicable disease and public health/PHLS, 2003. 6:106-12.
4. Ott, J. J., et al., Global epidemiology of hepatitis B virus infection: new estimates of age-specific HBsAg seroprevalence and endemicity. Vaccine 2012. 30:2212-9.
5. Weinbaum C M, Williams I, Mast E E, et al. Recommendations for identification and public health management of persons with chronic hepatitis B virus infection. Centers for Disease Control and Prevention (CDC). MMWR Recomm Rep. 2008. 57(RR-8):1-20.
6. Wasley A, Kruszon-Moran D, Kuhnert W, et al. The prevalence of hepatitis B virus infection in the United States in the era of vaccination. J Infect Dis. 2010. 202:192-201.

7. Mitchell T, Armstrong G L, Hu D J, Wasley A, Painter J A. The increasing burden of imported chronic hepatitis B-United States, 1974-2008. PLoS One. 2011. 6:e27717.
8. Hepatitis B vaccines. Releve epidemiologique hebdomadaire/Section d'hygiene du Secretariat de la Societe des Nations=Weekly epidemiological record/Health Section of the Secretariat of the League of Nations, 2004. 79:255-63.
9. Perz J F et al., The contributions of hepatitis B virus and hepatitis C virus infections to cirrhosis and primary liver cancer worldwide. J Hepatol 2006. 45:529-38.
10. Lavanchy, D., Hepatitis B virus epidemiology, disease burden, treatment, and current and emerging prevention and control measures. J Viral Hep 2004. 11:97-107.
11. Kim W R, Epidemiology of hepatitis B in the United States. Hepatology, 2009. 49: S28-34.
12. Wang L, Zou Z Q, Liu C X, Liu X Z. Immunotherapeutic interventions in chronic hepatitis B virus infection: a review. J Immunol Methods. 2014 May; 407:1-8.
13. Thai H, Campo D S, Lara J, et al. Convergence and coevolution of hepatitis B virus drug resistance. Nat Commun. 2012. 3:789.
14. Menéndez-Arias L, Alvarez M, Pacheco B. Nucleoside/nucleotide analog inhibitors of hepatitis B virus polymerase: mechanism of action and resistance. Curr Opin Virol. 2014. 8C:1-9.
15. Wiegand J, van Bommel F, Berg T. Management of chronic hepatitis B: status and challenges beyond treatment guidelines. Semin Liver Dis 2010; 30:361-377.
16. Luckhaupt S E, Calvert G M. Deaths due to bloodborne infections and their sequelae among health-care workers. Am J Ind Med. 2008. 51:812-24.
17. Beck, J. and M. Nassal, Hepatitis B virus replication. World J Gastroenterol WJG, 2007. 13:48-64.
18. Maini M K, Boni C, Lee C K, Larrubia J R, Reignat S, Ogg G S, et al. The role of virus-specific CD8(+) cells in liver damage and viral control during persistent hepatitis B virus infection. J Exp Med 2000; 191:1269-1280.
19. Akbar S M, Chen S, Al-Mahtab M, Abe M, Hiasa Y, Onji M. Strong and multi-antigen specific immunity by hepatitis B core antigen (HBcAg)-based vaccines in a murine model of chronic hepatitis B: HBcAg is a candidate for a therapeutic vaccine against hepatitis B virus. Antiviral Res 2012; 96:59-64.
20. Cao W, Qiu Z, Zhu T, Li Y, Han Y, Li T. CD8+ T cell responses specific for hepatitis B virus core protein in patients with chronic hepatitis B virus infection. J Clin Virol. 2014. 61:40-6.
21. Penna A, Chisari F V, Bertoletti A, et al. Cytotoxic T lymphocytes recognize an HLA-A2-restricted epitope within the hepatitis B virus nucleocapsid antigen. J Exp Med. 1991. 174:1565-70.
22. Sun L, Zhang Y, Zhao B, et al. A new unconventional HLA-A2-restricted epitope from HBV core protein elicits antiviral cytotoxic T lymphocytes. Protein Cell. 2014. 5:317-27.
23. Valentine M A, Clark E A, Shu G L, Norris N A, Ledbetter J A. Antibody to a novel 95-kDa surface glycoprotein on human B cells induces calcium mobilization and B cell activation. J Immunol. 1988. 140:4071-8.
24. Miyake, K., et al., Murine B cell proliferation and protection from apoptosis with an antibody against a 105-kD molecule: unresponsiveness of X-linked immunodeficient B cells. J Exp Med 1994. 180:1217-24.
25. Miyake, K., et al., RP105, a novel B cell surface molecule implicated in B cell activation, is a member of the leucine-rich repeat protein family. J Immunol 1995. 154:3333-40.
26. Alving C R, Peachman K K, Rao M, Reed S G. *Adjuvants for human vaccines*. Curr Opin Immunol. 2012. 24:310-5.
27. Shimazu, R., et al., MD-2, a molecule that confers lipopolysaccharide responsiveness on Toll-like receptor 4. J Exp Med 1999. 189:1777-82.
28. Hebeis, B., et al., Vav proteins are required for B-lymphocyte responses to LPS. Blood, 2005. 106:635-40.
29. Hebeis, B. J., et al., Activation of virus-specific memory B cells in the absence of T cell help. J Exp Med 2004. 199:593-602.
30. Yazawa, N., et al., CD19 regulates innate immunity by the toll-like receptor RP105 signaling in B lymphocytes. Blood, 2003. 102:1374-80.
31. Chaplin, J. W., et al., Anti-CD180 (RP105) activates B cells to rapidly produce polyclonal Ig via a T cell and MyD88-independent pathway. J Immunol, 2011. 187: 4199-209.
32. Chaplin J W, Chappell C P, Clark E A. Targeting antigens to CD180 rapidly induces antigen-specific IgG, affinity maturation and immunologic memory. 2013. J Exp Med 210:2135-46.
33. Ramos, H. J. and M. Gale, Jr., RIG-I like receptors and their signaling crosstalk in the regulation of antiviral immunity. Curr Opin Virol, 2011. 1:67-76.
34. Maxon E R, Siegrist C A. The next decade of vaccines: societal and scientific challenges. Lancet. 2011. 378:348-59.
35. Liang Y et al., Predictors of relapse in chronic hepatitis B after discontinuation of antiviral therapy. Aliment Pharmacol Ther, 2011. 34:344-52.
36. Suthar M S, Diamond M S, Gale M, Jr. West Nile virus infection and immunity. 2013. Nat Rev Microbiol 11:115-128.
37. Coffman R L, Sher A, Seder R A. Vaccine adjuvants: putting innate immunity to work. Immunity. 2010. 33:492-503.
38. Bourne C R, Katen S P, Fulz M R, Packianathan C, Zlotnick A. A mutant hepatitis B virus core protein mimics inhibitors of icosahedral capsid self-assembly. Biochemistry. 2009. 48:1736-1742.
39. Packianathan C, Katen S P, Dann C E, 3rd, Zlotnick A. Conformational changes in the hepatitis B virus core protein are consistent with a role for allostery in virus assembly. J Virol. 2010. 84:1607-1615.
40. Clark E A, Shu G L, Lischer B, Draves K E, Banchereau J, Ledbetter J A, Valentine M A. Activation of human B cells. Comparison of the signal transduced by IL-4 to four different competence signals. J Immunol. 1989. 143: 3873-80.
41. Loudon P T, Yager E J, Lynch D T, Narendran A, Stagnar C, Franchini A M, Fuller J T, White P A, Nyuandi J, Wiley C A, Murphey-Corb M, Fuller D H. GM-CSF increases mucosal and systemic immunogenicity of an H1 N1 influenza DNA vaccine administered into the epidermis of non-human primates. PLoS One. 2010. 5:e11021.

The invention claimed is:

1. A composition comprising a polypeptide comprising an amino acid sequence at least 90% identical to the amino acid sequence of SEQ ID NO:3 residues 1-418.

2. The composition of claim 1, wherein the polypeptide comprises the amino acid sequence of SEQ ID NO: 2, 3, 5, 6, 8, 9, 11, 12, 18, or 19.

3. The composition of claim 1, wherein the composition further comprises an adjuvant.

4. The composition of claim 3, wherein an adjuvant is selected from the group consisting of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, and oil-in-water emulsion.

5. A pharmaceutical composition, comprising
(a) the composition of claim 1; and
(b) a pharmaceutically acceptable carrier.

6. The composition of claim 1, wherein the polypeptide comprises an amino acid sequence at least 90% identical to the amino acid sequence of SEQ ID NO: 3.

7. The composition of claim 1, wherein the polypeptide comprises the amino acid sequence of SEQ ID NO:3 residues 1-418.

8. The composition of claim 1, wherein the polypeptide comprises the amino acid sequence of SEQ ID NO:3.

9. The composition of claim 1, wherein the polypeptide comprises the amino acid sequence of SEQ ID NO:2 residues 1-438.

10. The composition of claim 1, wherein the polypeptide comprises the amino acid sequence of SEQ ID NO:2.

11. The composition of claim 7, wherein the composition further comprises an adjuvant.

12. The composition of claim 11, wherein an adjuvant is selected from the group consisting of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, and oil-in-water emulsion.

13. The composition of claim 9, wherein the composition further comprises an adjuvant.

14. The composition of claim 13, wherein an adjuvant is selected from the group consisting of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, and oil-in-water emulsion.

15. A pharmaceutical composition, comprising
(a) the composition of claim 7; and
(b) a pharmaceutically acceptable carrier.

16. A pharmaceutical composition, comprising
(a) the composition of claim 9; and
(b) a pharmaceutically acceptable carrier.

* * * * *

SEQUENCE LISTING

<160> NUMBER OF SEQ ID NOS: 63

<210> SEQ ID NO 1
<211> LENGTH: 1365
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gcgaagcttt | gagccaccat | ggaaacccca | gcgcagcttc | tcttcctcct | gctactctgg | 60 |
| ctcccagata | ccaccggtga | catccagatg | actcagtctc | cagcctccct | atctgcatct | 120 |
| gtgggagaaa | ctgtcaccat | cacatgtcga | gcaagtgaga | gatttacag | ttatttagca | 180 |
| tggtatcagc | agaaacaggg | aaaatctcct | cagctcctgg | tctataacgc | aaaaacctta | 240 |
| gcagaaggtg | tgccatcaag | gttcagtgtc | agtggatcag | gcacacagtt | ttctctgagg | 300 |
| atcaacagcc | tgcagcctga | agattttggg | acttattact | gtcaacatca | ttttggttct | 360 |
| cctcggacgt | tcggtggagg | caccaaactg | gaaatcaaag | atctcggagg | aggtggctca | 420 |
| ggtggtggag | gatctggagg | aggtgggagt | ggtggaggtg | gttctaccgg | tgaggtccag | 480 |
| ctgcaacagt | ctggacctga | actggtgaag | cctggagctt | caatgaagat | atcctgcaag | 540 |
| gcttctggtt | actcattcac | tggctacacc | atgaactggg | tgaagcagag | ccatggaaag | 600 |
| accttgaat | ggattggact | tattaatcct | tacaatggtg | ttactagcta | caaccagaag | 660 |
| ttcaaggaca | aggccacatt | aactgtagac | aagtcatcca | gcacagccta | catggaactc | 720 |
| ctcagtctga | catctgagga | ctctgcaatc | tattactgtg | caagagacta | taattacgac | 780 |
| tactttgact | actggggcca | aggcaccact | ctcacagtct | cctcaggagg | aggtggctca | 840 |
| ggtggtggag | gatctggagg | aggtgggagt | ggtggaggtg | gttctatgga | cattgacccg | 900 |
| tataaagaat | ttggagcttc | tgtggagtta | ctctcttttt | tgccttctga | cttctttcct | 960 |
| tctattcgag | atctcctcga | caccgcctct | gctctgtatc | gggaggcctt | agagtctccg | 1020 |
| gaacattgtt | cacctcacca | tacagcactc | aggcaagcta | ttctgtgttg | gggtgagttg | 1080 |
| atgaatctgg | ccacctgggt | gggaagtaat | ttggaagacc | agcatccag | ggaattagta | 1140 |
| gtcagctatg | tcaatgttaa | tatgggccta | aaaattagac | aactattgtg | gtttcacatt | 1200 |
| tcctgcctta | cttttggaag | agaaactgtc | cttgagtatt | tggtgtcttt | tggagtgtgg | 1260 |
| attcgcactc | ctcccgctgc | cagaccacca | aatgccccta | tcttatcaac | acttccggaa | 1320 |
| actactgttg | ttcaccacca | tcatcatcat | tgataaggat | ccgcg | | 1365 |

<210> SEQ ID NO 2
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (439)..(444)
<223> OTHER INFORMATION: optionally absent

<400> SEQUENCE: 2

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Lys

```
                35                  40                  45
Ile Tyr Ser Tyr Leu Ala Trp Tyr Gln Gln Lys Gln Gly Lys Ser Pro
 50                  55                  60

Gln Leu Leu Val Tyr Asn Ala Lys Thr Leu Ala Glu Gly Val Pro Ser
 65                  70                  75                  80

Arg Phe Ser Val Ser Gly Ser Gly Thr Gln Phe Ser Leu Arg Ile Asn
                 85                  90                  95

Ser Leu Gln Pro Glu Asp Phe Gly Thr Tyr Tyr Cys Gln His His Phe
                100                 105                 110

Gly Ser Pro Arg Thr Phe Gly Gly Thr Lys Leu Glu Ile Lys Asp
            115                 120                 125

Leu Gly Gly Gly Gly Ser Gly Gly Gly Gly Ser Gly Gly Gly Gly Ser
130                 135                 140

Gly Gly Gly Gly Ser Thr Gly Glu Val Gln Leu Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190

Gly Lys Thr Leu Glu Trp Ile Gly Leu Ile Asn Pro Tyr Asn Gly Val
        195                 200                 205

Thr Ser Tyr Asn Gln Lys Phe Lys Asp Lys Ala Thr Leu Thr Val Asp
210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Gly Gly Gly
            260                 265                 270

Gly Ser Gly Gly Gly Gly Ser Gly Gly Gly Ser Gly Gly Gly Gly
        275                 280                 285

Ser Met Asp Ile Asp Pro Tyr Lys Glu Phe Gly Ala Ser Val Glu Leu
290                 295                 300

Leu Ser Phe Leu Pro Ser Asp Phe Phe Pro Ser Ile Arg Asp Leu Leu
305                 310                 315                 320

Asp Thr Ala Ser Ala Leu Tyr Arg Glu Ala Leu Glu Ser Pro Glu His
                325                 330                 335

Cys Ser Pro His His Thr Ala Leu Arg Gln Ala Ile Leu Cys Trp Gly
            340                 345                 350

Glu Leu Met Asn Leu Ala Thr Trp Val Gly Ser Asn Leu Glu Asp Pro
        355                 360                 365

Ala Ser Arg Glu Leu Val Val Ser Tyr Val Asn Val Asn Met Gly Leu
370                 375                 380

Lys Ile Arg Gln Leu Leu Trp Phe His Ile Ser Cys Leu Thr Phe Gly
385                 390                 395                 400

Arg Glu Thr Val Leu Glu Tyr Leu Val Ser Phe Gly Val Trp Ile Arg
                405                 410                 415

Thr Pro Pro Ala Ala Arg Pro Pro Asn Ala Pro Ile Leu Ser Thr Leu
            420                 425                 430

Pro Glu Thr Thr Val Val His His His His His
        435                 440

<210> SEQ ID NO 3
```

```
<211> LENGTH: 424
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (419)..(424)
<223> OTHER INFORMATION: optionally absent

<400> SEQUENCE: 3

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Lys Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Val
    50                  55                  60

Ser Gly Ser Gly Thr Gln Phe Ser Leu Arg Ile Asn Ser Leu Gln Pro
65                  70                  75                  80

Glu Asp Phe Gly Thr Tyr Tyr Cys Gln His His Phe Gly Ser Pro Arg
                85                  90                  95

Thr Phe Gly Gly Gly Thr Lys Leu Glu Ile Lys Asp Leu Gly Gly Gly
            100                 105                 110

Gly Ser Gly Gly Gly Gly Ser Gly Gly Gly Ser Gly Gly Gly Gly
        115                 120                 125

Ser Thr Gly Glu Val Gln Leu Gln Gln Ser Gly Pro Glu Leu Val Lys
130                 135                 140

Pro Gly Ala Ser Met Lys Ile Ser Cys Lys Ala Ser Gly Tyr Ser Phe
145                 150                 155                 160

Thr Gly Tyr Thr Met Asn Trp Val Lys Gln Ser His Gly Lys Thr Leu
                165                 170                 175

Glu Trp Ile Gly Leu Ile Asn Pro Tyr Asn Gly Val Thr Ser Tyr Asn
            180                 185                 190

Gln Lys Phe Lys Asp Lys Ala Thr Leu Thr Val Asp Lys Ser Ser Ser
        195                 200                 205

Thr Ala Tyr Met Glu Leu Leu Ser Leu Thr Ser Glu Asp Ser Ala Ile
    210                 215                 220

Tyr Tyr Cys Ala Arg Asp Tyr Asn Tyr Asp Tyr Phe Asp Tyr Trp Gly
225                 230                 235                 240

Gln Gly Thr Thr Leu Thr Val Ser Ser Gly Gly Gly Gly Ser Gly Gly
                245                 250                 255

Gly Gly Ser Gly Gly Gly Gly Ser Gly Gly Gly Gly Ser Met Asp Ile
            260                 265                 270

Asp Pro Tyr Lys Glu Phe Gly Ala Ser Val Glu Leu Leu Ser Phe Leu
        275                 280                 285

Pro Ser Asp Phe Phe Pro Ser Ile Arg Asp Leu Leu Asp Thr Ala Ser
    290                 295                 300

Ala Leu Tyr Arg Glu Ala Leu Glu Ser Pro Glu His Cys Ser Pro His
305                 310                 315                 320

His Thr Ala Leu Arg Gln Ala Ile Leu Cys Trp Gly Glu Leu Met Asn
                325                 330                 335

Leu Ala Thr Trp Val Gly Ser Asn Leu Glu Asp Pro Ala Ser Arg Glu
            340                 345                 350

Leu Val Val Ser Tyr Val Asn Val Asn Met Gly Leu Lys Ile Arg Gln
```

```
                    355                 360                 365

Leu Leu Trp Phe His Ile Ser Cys Leu Thr Phe Gly Arg Glu Thr Val
    370                 375                 380

Leu Glu Tyr Leu Val Ser Phe Gly Val Trp Ile Arg Thr Pro Pro Ala
385                 390                 395                 400

Ala Arg Pro Pro Asn Ala Pro Ile Leu Ser Thr Leu Pro Glu Thr Thr
                405                 410                 415

Val Val His His His His His His
            420

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Gly Gly Gly Gly Ser Gly Gly Gly Ser Gly Gly Gly Gly Ser Gly
1               5                   10                  15

Gly Gly Gly Ser
            20

<210> SEQ ID NO 5
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (439)..(444)
<223> OTHER INFORMATION: optionally absent

<400> SEQUENCE: 5

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Lys
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65              70                  75                  80

Arg Phe Ser Val Ser Gly Ser Gly Thr Gln Phe Ser Leu Arg Ile Asn
                85                  90                  95

Ser Leu Gln Pro Glu Asp Phe Gly Thr Tyr Tyr Cys His His Phe
            100                 105                 110

Gly Ser Pro Arg Thr Phe Gly Gly Gly Thr Lys Leu Glu Ile Lys Asp
        115                 120                 125

Leu Gly Gly Gly Gly Ser Gly Gly Gly Gly Ser Gly Gly Gly Gly Ser
    130                 135                 140

Gly Gly Gly Gly Ser Thr Gly Glu Val Gln Leu Gln Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190
```

Gly Lys Thr Leu Glu Trp Ile Gly Leu Ile Asn Pro Tyr Asn Gly Val
              195                 200                 205

Thr Ser Tyr Asn Gln Lys Phe Lys Asp Lys Ala Thr Leu Thr Val Asp
    210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Gly Gly Gly
            260                 265                 270

Gly Ser Gly Gly Gly Ser Gly Gly Gly Ser Gly Gly Gly Gly
        275                 280                 285

Ser Met Asp Ile Asp Pro Tyr Lys Glu Phe Gly Ala Ser Val Glu Leu
    290                 295                 300

Leu Ser Phe Leu Pro Ser Asp Phe Phe Pro Ser Ile Arg Asp Leu Leu
305                 310                 315                 320

Asp Thr Ala Ser Ala Leu Tyr Arg Glu Ala Leu Glu Ser Pro Glu His
                325                 330                 335

Cys Ser Pro His His Thr Ala Leu Arg Gln Ala Ile Leu Cys Trp Gly
            340                 345                 350

Glu Leu Met Asn Leu Ala Thr Trp Val Gly Ser Asn Leu Glu Asp Pro
        355                 360                 365

Ala Ser Arg Glu Leu Val Val Ser Tyr Val Asn Val Asn Met Gly Leu
    370                 375                 380

Lys Ile Arg Gln Leu Leu Trp Phe His Ile Ser Cys Leu Thr Phe Gly
385                 390                 395                 400

Arg Glu Thr Val Leu Glu Tyr Leu Val Ser Phe Gly Val Trp Ile Arg
                405                 410                 415

Thr Pro Pro Ala Tyr Arg Pro Pro Asn Ala Pro Ile Leu Ser Thr Leu
            420                 425                 430

Pro Glu Thr Thr Val Val His His His His His
        435                 440

<210> SEQ ID NO 6
<211> LENGTH: 424
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (419)..(424)
<223> OTHER INFORMATION: optionally absent

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Lys Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Val
    50                  55                  60

Ser Gly Ser Gly Thr Gln Phe Ser Leu Arg Ile Asn Ser Leu Gln Pro
65                  70                  75                  80

Glu Asp Phe Gly Thr Tyr Tyr Cys Gln His His Phe Gly Ser Pro Arg

```
                    85                  90                  95
Thr Phe Gly Gly Gly Thr Lys Leu Glu Ile Lys Asp Leu Gly Gly Gly
                100                 105                 110
Gly Ser Gly Gly Gly Ser Gly Gly Gly Ser Gly Gly Gly
        115                 120                 125
Ser Thr Gly Glu Val Gln Leu Gln Gln Ser Gly Pro Glu Leu Val Lys
        130                 135                 140
Pro Gly Ala Ser Met Lys Ile Ser Cys Lys Ala Ser Gly Tyr Ser Phe
145                 150                 155                 160
Thr Gly Tyr Thr Met Asn Trp Val Lys Gln Ser His Gly Lys Thr Leu
                165                 170                 175
Glu Trp Ile Gly Leu Ile Asn Pro Tyr Asn Gly Val Thr Ser Tyr Asn
            180                 185                 190
Gln Lys Phe Lys Asp Lys Ala Thr Leu Thr Val Asp Lys Ser Ser Ser
        195                 200                 205
Thr Ala Tyr Met Glu Leu Leu Ser Leu Thr Ser Glu Asp Ser Ala Ile
        210                 215                 220
Tyr Tyr Cys Ala Arg Asp Tyr Asn Tyr Asp Tyr Phe Asp Tyr Trp Gly
225                 230                 235                 240
Gln Gly Thr Thr Leu Thr Val Ser Ser Gly Gly Gly Ser Gly Gly
                245                 250                 255
Gly Gly Ser Gly Gly Gly Gly Ser Gly Gly Gly Ser Met Asp Ile
            260                 265                 270
Asp Pro Tyr Lys Glu Phe Gly Ala Ser Val Glu Leu Leu Ser Phe Leu
        275                 280                 285
Pro Ser Asp Phe Phe Pro Ser Ile Arg Asp Leu Leu Asp Thr Ala Ser
        290                 295                 300
Ala Leu Tyr Arg Glu Ala Leu Glu Ser Pro Glu His Cys Ser Pro His
305                 310                 315                 320
His Thr Ala Leu Arg Gln Ala Ile Leu Cys Trp Gly Glu Leu Met Asn
                325                 330                 335
Leu Ala Thr Trp Val Gly Ser Asn Leu Glu Asp Pro Ala Ser Arg Glu
            340                 345                 350
Leu Val Val Ser Tyr Val Asn Val Asn Met Gly Leu Lys Ile Arg Gln
        355                 360                 365
Leu Leu Trp Phe His Ile Ser Cys Leu Thr Phe Gly Arg Glu Thr Val
        370                 375                 380
Leu Glu Tyr Leu Val Ser Phe Gly Val Trp Ile Arg Thr Pro Pro Ala
385                 390                 395                 400
Tyr Arg Pro Pro Asn Ala Pro Ile Leu Ser Thr Leu Pro Glu Thr Thr
                405                 410                 415
Val Val His His His His His
            420

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Asp Phe Leu Val Ile Tyr Ile Glu Glu Ala His Ala Ser Asp Gly Trp
1               5                   10                  15
```

```
<210> SEQ ID NO 8
<211> LENGTH: 474
<212> TYPE: PRT
<213> ORGANISM: Artificial Sequence
<220> FEATURE:
<223> OTHER INFORMATION: Synthetic
<220> FEATURE:
<221> NAME/KEY: INIT_MET
<222> LOCATION: (469)..(474)
<223> OTHER INFORMATION: optionally absent

<400> SEQUENCE: 8
```

Met Glu Thr Pro Ala Gln Leu Leu Phe Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Lys
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Val Ser Gly Ser Gly Thr Gln Phe Ser Leu Arg Ile Asn
                85                  90                  95

Ser Leu Gln Pro Glu Asp Phe Gly Thr Tyr Tyr Cys Gln His His Phe
            100                 105                 110

Gly Ser Pro Arg Thr Phe Gly Gly Gly Thr Lys Leu Glu Ile Lys Asp
        115                 120                 125

Leu Gly Gly Gly Gly Ser Gly Gly Gly Ser Gly Gly Gly Gly Ser
    130                 135                 140

Gly Gly Gly Gly Ser Thr Gly Glu Val Gln Leu Gln Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190

Gly Lys Thr Leu Glu Trp Ile Gly Leu Ile Asn Pro Tyr Asn Gly Val
        195                 200                 205

Thr Ser Tyr Asn Gln Lys Phe Lys Asp Lys Ala Thr Leu Thr Val Asp
    210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Gly Gly Gly
            260                 265                 270

Gly Ser Gly Gly Gly Gly Ser Gly Gly Gly Ser Gly Gly Gly Gly
        275                 280                 285

Ser Met Asp Ile Asp Pro Tyr Lys Glu Phe Gly Ala Ser Val Glu Leu
    290                 295                 300

Leu Ser Phe Leu Pro Ser Asp Phe Phe Pro Ser Ile Arg Asp Leu Leu
305                 310                 315                 320

Asp Thr Ala Ser Ala Leu Tyr Arg Glu Ala Leu Glu Ser Pro Glu His
                325                 330                 335

Cys Ser Pro His His Thr Ala Leu Arg Gln Ala Ile Leu Cys Trp Gly
            340                 345                 350

```
Glu Leu Met Asn Leu Ala Thr Trp Val Gly Ser Asn Leu Glu Asp Pro
            355                 360                 365

Ala Ser Arg Glu Leu Val Val Ser Tyr Val Asn Val Asn Met Gly Leu
370                 375                 380

Lys Ile Arg Gln Leu Leu Trp Phe His Ile Ser Cys Leu Thr Phe Gly
385                 390                 395                 400

Arg Glu Thr Val Leu Glu Tyr Leu Val Ser Phe Gly Val Trp Ile Arg
                405                 410                 415

Thr Pro Pro Ala Ala Arg Pro Pro Asn Ala Pro Ile Leu Ser Thr Leu
            420                 425                 430

Pro Glu Thr Thr Val Val Arg Arg Gly Arg Ser Pro Arg Arg Arg
            435                 440                 445

Thr Pro Ser Pro Arg Arg Arg Ser Gln Ser Pro Arg Arg Arg
450                 455                 460

Ser Gln Ser Arg His His His His His His
465                 470

<210> SEQ ID NO 9
<211> LENGTH: 454
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (449)..(454)
<223> OTHER INFORMATION: optionally absent

<400> SEQUENCE: 9

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Lys Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Val
50                  55                  60

Ser Gly Ser Gly Thr Gln Phe Ser Leu Arg Ile Asn Ser Leu Gln Pro
65                  70                  75                  80

Glu Asp Phe Gly Thr Tyr Tyr Cys Gln His His Phe Gly Ser Pro Arg
                85                  90                  95

Thr Phe Gly Gly Gly Thr Lys Leu Glu Ile Lys Asp Leu Gly Gly Gly
            100                 105                 110

Gly Ser Gly Gly Gly Gly Ser Gly Gly Gly Ser Gly Gly Gly Gly
        115                 120                 125

Ser Thr Gly Glu Val Gln Leu Gln Gln Ser Gly Pro Glu Leu Val Lys
130                 135                 140

Pro Gly Ala Ser Met Lys Ile Ser Cys Lys Ala Ser Gly Tyr Ser Phe
145                 150                 155                 160

Thr Gly Tyr Thr Met Asn Trp Val Lys Gln Ser His Gly Lys Thr Leu
                165                 170                 175

Glu Trp Ile Gly Leu Ile Asn Pro Tyr Asn Gly Val Thr Ser Tyr Asn
            180                 185                 190

Gln Lys Phe Lys Asp Lys Ala Thr Leu Thr Val Asp Lys Ser Ser Ser
        195                 200                 205

Thr Ala Tyr Met Glu Leu Leu Ser Leu Thr Ser Glu Asp Ser Ala Ile
210                 215                 220
```

```
Tyr Tyr Cys Ala Arg Asp Tyr Asn Tyr Asp Tyr Phe Asp Tyr Trp Gly
225                 230                 235                 240

Gln Gly Thr Thr Leu Thr Val Ser Ser Gly Gly Gly Gly Ser Gly Gly
            245                 250                 255

Gly Gly Ser Gly Gly Gly Gly Ser Gly Gly Gly Gly Ser Met Asp Ile
        260                 265                 270

Asp Pro Tyr Lys Glu Phe Gly Ala Ser Val Glu Leu Leu Ser Phe Leu
    275                 280                 285

Pro Ser Asp Phe Phe Pro Ser Ile Arg Asp Leu Leu Asp Thr Ala Ser
290                 295                 300

Ala Leu Tyr Arg Glu Ala Leu Glu Ser Pro Glu His Cys Ser Pro His
305                 310                 315                 320

His Thr Ala Leu Arg Gln Ala Ile Leu Cys Trp Gly Glu Leu Met Asn
            325                 330                 335

Leu Ala Thr Trp Val Gly Ser Asn Leu Glu Asp Pro Ala Ser Arg Glu
        340                 345                 350

Leu Val Val Ser Tyr Val Asn Val Asn Met Gly Leu Lys Ile Arg Gln
    355                 360                 365

Leu Leu Trp Phe His Ile Ser Cys Leu Thr Phe Gly Arg Glu Thr Val
370                 375                 380

Leu Glu Tyr Leu Val Ser Phe Gly Val Trp Ile Arg Thr Pro Pro Ala
385                 390                 395                 400

Ala Arg Pro Pro Asn Ala Pro Ile Leu Ser Thr Leu Pro Glu Thr Thr
            405                 410                 415

Val Val Arg Arg Arg Gly Arg Ser Pro Arg Arg Arg Thr Pro Ser Pro
        420                 425                 430

Arg Arg Arg Arg Ser Gln Ser Pro Arg Arg Arg Arg Ser Gln Ser Arg
    435                 440                 445

His His His His His His
    450

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Gln Gly Pro Lys Glu Pro Phe Arg Asp Tyr Val Asp Arg Phe Tyr Lys
1               5                   10                  15

Thr Leu Arg Ala
            20

<210> SEQ ID NO 11
<211> LENGTH: 474
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (469)..(474)
<223> OTHER INFORMATION: optionally absent

<400> SEQUENCE: 11

Met Glu Thr Pro Ala Gln Leu Leu Phe Leu Leu Leu Leu Trp Leu Pro
1               5                   10                  15
```

```
Asp Thr Thr Gly Asp Ile Gln Met Thr Gln Ser Pro Ala Ser Leu Ser
                20                  25                  30
Ala Ser Val Gly Glu Thr Val Thr Ile Thr Cys Arg Ala Ser Glu Lys
            35                  40                  45
Ile Tyr Ser Tyr Leu Ala Trp Tyr Gln Gln Lys Gln Gly Lys Ser Pro
        50                  55                  60
Gln Leu Leu Val Tyr Asn Ala Lys Thr Leu Ala Glu Gly Val Pro Ser
 65                 70                  75                  80
Arg Phe Ser Val Ser Gly Ser Gly Thr Gln Phe Ser Leu Arg Ile Asn
                85                  90                  95
Ser Leu Gln Pro Glu Asp Phe Gly Thr Tyr Tyr Cys Gln His His Phe
            100                 105                 110
Gly Ser Pro Arg Thr Phe Gly Gly Gly Thr Lys Leu Glu Ile Lys Asp
        115                 120                 125
Leu Gly Gly Gly Gly Ser Gly Gly Gly Gly Ser Gly Gly Gly Gly Ser
    130                 135                 140
Gly Gly Gly Gly Ser Thr Gly Glu Val Gln Leu Gln Gln Ser Gly Pro
145                 150                 155                 160
Glu Leu Val Lys Pro Gly Ala Ser Met Lys Ile Ser Cys Lys Ala Ser
                165                 170                 175
Gly Tyr Ser Phe Thr Gly Tyr Thr Met Asn Trp Val Lys Gln Ser His
            180                 185                 190
Gly Lys Thr Leu Glu Trp Ile Gly Leu Ile Asn Pro Tyr Asn Gly Val
        195                 200                 205
Thr Ser Tyr Asn Gln Lys Phe Lys Asp Lys Ala Thr Leu Thr Val Asp
    210                 215                 220
Lys Ser Ser Ser Thr Ala Tyr Met Glu Leu Leu Ser Leu Thr Ser Glu
225                 230                 235                 240
Asp Ser Ala Ile Tyr Tyr Cys Ala Arg Asp Tyr Asn Tyr Asp Tyr Phe
                245                 250                 255
Asp Tyr Trp Gly Gln Gly Thr Thr Leu Thr Val Ser Ser Gly Gly Gly
            260                 265                 270
Gly Ser Gly Gly Gly Gly Ser Gly Gly Gly Gly Ser Gly Gly Gly Gly
        275                 280                 285
Ser Met Asp Ile Asp Pro Tyr Lys Glu Phe Gly Ala Ser Val Glu Leu
    290                 295                 300
Leu Ser Phe Leu Pro Ser Asp Phe Phe Pro Ser Ile Arg Asp Leu Leu
305                 310                 315                 320
Asp Thr Ala Ser Ala Leu Tyr Arg Glu Ala Leu Glu Ser Pro Glu His
                325                 330                 335
Cys Ser Pro His His Thr Ala Leu Arg Gln Ala Ile Leu Cys Trp Gly
            340                 345                 350
Glu Leu Met Asn Leu Ala Thr Trp Val Gly Ser Asn Leu Glu Asp Pro
        355                 360                 365
Ala Ser Arg Glu Leu Val Val Ser Tyr Val Asn Val Asn Met Gly Leu
    370                 375                 380
Lys Ile Arg Gln Leu Leu Trp Phe His Ile Ser Cys Leu Thr Phe Gly
385                 390                 395                 400
Arg Glu Thr Val Leu Glu Tyr Leu Val Ser Phe Gly Val Trp Ile Arg
                405                 410                 415
Thr Pro Pro Ala Tyr Arg Pro Pro Asn Ala Pro Ile Leu Ser Thr Leu
            420                 425                 430
Pro Glu Thr Thr Val Val Arg Arg Arg Gly Arg Ser Pro Arg Arg Arg
```

```
                   435                 440                 445
Thr Pro Ser Pro Arg Arg Arg Ser Gln Ser Pro Arg Arg Arg Arg
    450                 455                 460

Ser Gln Ser Arg His His His His His His
465                 470

<210> SEQ ID NO 12
<211> LENGTH: 454
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (449)..(454)
<223> OTHER INFORMATION: optionally absent

<400> SEQUENCE: 12

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Lys Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Val
50                  55                  60

Ser Gly Ser Gly Thr Gln Phe Ser Leu Arg Ile Asn Ser Leu Gln Pro
65                  70                  75                  80

Glu Asp Phe Gly Thr Tyr Tyr Cys Gln His His Phe Gly Ser Pro Arg
                85                  90                  95

Thr Phe Gly Gly Gly Thr Lys Leu Glu Ile Lys Asp Leu Gly Gly Gly
            100                 105                 110

Gly Ser Gly Gly Gly Gly Ser Gly Gly Gly Ser Gly Gly Gly Gly
        115                 120                 125

Ser Thr Gly Glu Val Gln Leu Gln Gln Ser Gly Pro Glu Leu Val Lys
130                 135                 140

Pro Gly Ala Ser Met Lys Ile Ser Cys Lys Ala Ser Gly Tyr Ser Phe
145                 150                 155                 160

Thr Gly Tyr Thr Met Asn Trp Val Lys Gln Ser His Gly Lys Thr Leu
                165                 170                 175

Glu Trp Ile Gly Leu Ile Asn Pro Tyr Asn Gly Val Thr Ser Tyr Asn
            180                 185                 190

Gln Lys Phe Lys Asp Lys Ala Thr Leu Thr Val Asp Lys Ser Ser Ser
        195                 200                 205

Thr Ala Tyr Met Glu Leu Leu Ser Leu Thr Ser Glu Asp Ser Ala Ile
210                 215                 220

Tyr Tyr Cys Ala Arg Asp Tyr Asn Tyr Asp Tyr Phe Asp Tyr Trp Gly
225                 230                 235                 240

Gln Gly Thr Thr Leu Thr Val Ser Ser Gly Gly Gly Ser Gly Gly
                245                 250                 255

Gly Gly Ser Gly Gly Gly Gly Ser Gly Gly Gly Gly Ser Met Asp Ile
            260                 265                 270

Asp Pro Tyr Lys Glu Phe Gly Ala Ser Val Glu Leu Leu Ser Phe Leu
        275                 280                 285

Pro Ser Asp Phe Phe Pro Ser Ile Arg Asp Leu Leu Asp Thr Ala Ser
290                 295                 300
```

```
Ala Leu Tyr Arg Glu Ala Leu Glu Ser Pro Glu His Cys Ser Pro His
305                 310                 315                 320

His Thr Ala Leu Arg Gln Ala Ile Leu Cys Trp Gly Glu Leu Met Asn
            325                 330                 335

Leu Ala Thr Trp Val Gly Ser Asn Leu Glu Asp Pro Ala Ser Arg Glu
        340                 345                 350

Leu Val Val Ser Tyr Val Asn Val Asn Met Gly Leu Lys Ile Arg Gln
    355                 360                 365

Leu Leu Trp Phe His Ile Ser Cys Leu Thr Phe Gly Arg Glu Thr Val
370                 375                 380

Leu Glu Tyr Leu Val Ser Phe Gly Val Trp Ile Arg Thr Pro Pro Ala
385                 390                 395                 400

Tyr Arg Pro Pro Asn Ala Pro Ile Leu Ser Thr Leu Pro Glu Thr Thr
                405                 410                 415

Val Val Arg Arg Arg Gly Arg Ser Pro Arg Arg Arg Thr Pro Ser Pro
            420                 425                 430

Arg Arg Arg Arg Ser Gln Ser Pro Arg Arg Arg Arg Ser Gln Ser Arg
            435                 440                 445

His His His His His His
        450

<210> SEQ ID NO 13
<211> LENGTH: 179
<212> TYPE: PRT
<213> ORGANISM: Artificial Sequence
<220> FEATURE:
<223> OTHER INFORMATION: Synthetic

<400> SEQUENCE: 13

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg

<210> SEQ ID NO 14
<211> LENGTH: 179
<212> TYPE: PRT
```

<213> ORGANISM: Artificial Sequence
<220> FEATURE:
<223> OTHER INFORMATION: Synthetic

<400> SEQUENCE: 14

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Ala Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg
```

<210> SEQ ID NO 15
<211> LENGTH: 149
<212> TYPE: PRT
<213> ORGANISM: Artificial Sequence
<220> FEATURE:
<223> OTHER INFORMATION: Synthetic

<400> SEQUENCE: 15

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145
```

<210> SEQ ID NO 16
<211> LENGTH: 149
<212> TYPE: PRT
<213> ORGANISM: Artificial Sequence
<220> FEATURE:
<223> OTHER INFORMATION: Synthetic

<400> SEQUENCE: 16

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Ala Arg Pro Pro Asn Ala Pro Ile Leu Ser Thr Leu Pro
    130                 135                 140

Glu Thr Thr Val Val
145
```

<210> SEQ ID NO 17
<211> LENGTH: 159
<212> TYPE: PRT
<213> ORGANISM: Artificial Sequence
<220> FEATURE:
<223> OTHER INFORMATION: Synthetic

<400> SEQUENCE: 17

```
Ser Lys Leu Cys Leu Gly Trp Leu Trp Gly Met Asp Ile Asp Pro Tyr
1               5                   10                  15

Lys Glu Phe Gly Ala Ser Val Glu Leu Leu Ser Phe Leu Pro Ser Asp
                20                  25                  30

Phe Phe Pro Ser Ile Arg Asp Leu Leu Asp Thr Ala Ser Ala Leu Tyr
            35                  40                  45

Arg Glu Ala Leu Glu Ser Pro Glu His Cys Ser Pro His His Thr Ala
        50                  55                  60

Leu Arg Gln Ala Ile Leu Cys Trp Gly Glu Leu Met Asn Leu Ala Thr
65                  70                  75                  80

Trp Val Gly Ser Asn Leu Glu Asp Pro Ala Ser Arg Glu Leu Val Val
                85                  90                  95

Ser Tyr Val Asn Val Asn Met Gly Leu Lys Ile Arg Gln Leu Leu Trp
            100                 105                 110

Phe His Ile Ser Cys Leu Thr Phe Gly Arg Glu Thr Val Leu Glu Tyr
        115                 120                 125

Leu Val Ser Phe Gly Val Trp Ile Arg Thr Pro Pro Ala Tyr Arg Pro
    130                 135                 140
```

Pro Asn Ala Pro Ile Leu Ser Thr Leu Pro Glu Thr Thr Val Val
145                 150                 155

<210> SEQ ID NO 18
<211> LENGTH: 454
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (449)..(454)
<223> OTHER INFORMATION: optionally absent

<400> SEQUENCE: 18

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Lys
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Val Ser Gly Ser Gly Thr Gln Phe Ser Leu Arg Ile Asn
                85                  90                  95

Ser Leu Gln Pro Glu Asp Phe Gly Thr Tyr Tyr Cys Gln His His Phe
            100                 105                 110

Gly Ser Pro Arg Thr Phe Gly Gly Gly Thr Lys Leu Glu Ile Lys Asp
        115                 120                 125

Leu Gly Gly Gly Gly Ser Gly Gly Gly Ser Gly Gly Gly Gly Gly Ser
    130                 135                 140

Gly Gly Gly Gly Ser Thr Gly Glu Val Gln Leu Gln Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190

Gly Lys Thr Leu Glu Trp Ile Gly Leu Ile Asn Pro Tyr Asn Gly Val
        195                 200                 205

Thr Ser Tyr Asn Gln Lys Phe Lys Asp Lys Ala Thr Leu Thr Val Asp
    210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Gly Gly Gly
            260                 265                 270

Gly Ser Gly Gly Gly Gly Ser Gly Gly Gly Gly Ser Gly Gly Gly Gly
        275                 280                 285

Ser Ser Lys Leu Cys Leu Gly Trp Leu Trp Gly Met Asp Ile Asp Pro
    290                 295                 300

Tyr Lys Glu Phe Gly Ala Ser Val Glu Leu Leu Ser Phe Leu Pro Ser
305                 310                 315                 320

Asp Phe Phe Pro Ser Ile Arg Asp Leu Leu Asp Thr Ala Ser Ala Leu
                325                 330                 335

```
Tyr Arg Glu Ala Leu Glu Ser Pro Glu His Cys Ser Pro His His Thr
                340                 345                 350
Ala Leu Arg Gln Ala Ile Leu Cys Trp Gly Leu Met Asn Leu Ala
            355                 360                 365
Thr Trp Val Gly Ser Asn Leu Glu Asp Pro Ala Ser Arg Glu Leu Val
    370                 375                 380
Val Ser Tyr Val Asn Val Asn Met Gly Leu Lys Ile Arg Gln Leu Leu
385                 390                 395                 400
Trp Phe His Ile Ser Cys Leu Thr Phe Gly Arg Glu Thr Val Leu Glu
                405                 410                 415
Tyr Leu Val Ser Phe Gly Val Trp Ile Arg Thr Pro Ala Tyr Arg
            420                 425                 430
Pro Pro Asn Ala Pro Ile Leu Ser Thr Leu Pro Glu Thr Thr Val Val
            435                 440                 445
His His His His His His
        450

<210> SEQ ID NO 19
<211> LENGTH: 434
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (429)..(434)
<223> OTHER INFORMATION: optionally absent

<400> SEQUENCE: 19

Asp Ile Gln Met Thr Gln Ser Pro Ala Ser Leu Ser Ala Ser Val Gly
1               5                   10                  15
Glu Thr Val Thr Ile Thr Cys Arg Ala Ser Glu Lys Ile Tyr Ser Tyr
            20                  25                  30
Leu Ala Trp Tyr Gln Gln Lys Gln Gly Lys Ser Pro Gln Leu Leu Val
        35                  40                  45
Tyr Asn Ala Lys Thr Leu Ala Glu Gly Val Pro Ser Arg Phe Ser Val
    50                  55                  60
Ser Gly Ser Gly Thr Gln Phe Ser Leu Arg Ile Asn Ser Leu Gln Pro
65                  70                  75                  80
Glu Asp Phe Gly Thr Tyr Tyr Cys Gln His Phe Gly Ser Pro Arg
                85                  90                  95
Thr Phe Gly Gly Gly Thr Lys Leu Glu Ile Lys Asp Leu Gly Gly Gly
            100                 105                 110
Gly Ser Gly Gly Gly Gly Ser Gly Gly Gly Gly Ser Gly Gly Gly Gly
        115                 120                 125
Ser Thr Gly Glu Val Gln Leu Gln Gln Ser Gly Pro Glu Leu Val Lys
    130                 135                 140
Pro Gly Ala Ser Met Lys Ile Ser Cys Lys Ala Ser Gly Tyr Ser Phe
145                 150                 155                 160
Thr Gly Tyr Thr Met Asn Trp Val Lys Gln Ser His Gly Lys Thr Leu
                165                 170                 175
Glu Trp Ile Gly Leu Ile Asn Pro Tyr Asn Gly Val Thr Ser Tyr Asn
            180                 185                 190
Gln Lys Phe Lys Asp Lys Ala Thr Leu Thr Val Asp Lys Ser Ser Ser
        195                 200                 205
Thr Ala Tyr Met Glu Leu Leu Ser Leu Thr Ser Glu Asp Ser Ala Ile
```

```
                    210                 215                 220
Tyr Tyr Cys Ala Arg Asp Tyr Asn Tyr Asp Tyr Phe Asp Tyr Trp Gly
225                 230                 235                 240

Gln Gly Thr Thr Leu Thr Val Ser Ser Gly Gly Gly Ser Gly Gly
                245                 250                 255

Gly Gly Ser Gly Gly Gly Ser Gly Gly Gly Ser Ser Lys Leu
            260                 265                 270

Cys Leu Gly Trp Leu Trp Gly Met Asp Ile Asp Pro Tyr Lys Glu Phe
            275                 280                 285

Gly Ala Ser Val Glu Leu Leu Ser Phe Leu Pro Ser Asp Phe Phe Pro
            290                 295                 300

Ser Ile Arg Asp Leu Leu Asp Thr Ala Ser Ala Leu Tyr Arg Glu Ala
305                 310                 315                 320

Leu Glu Ser Pro Glu His Cys Ser Pro His His Thr Ala Leu Arg Gln
                325                 330                 335

Ala Ile Leu Cys Trp Gly Glu Leu Met Asn Leu Ala Thr Trp Val Gly
            340                 345                 350

Ser Asn Leu Glu Asp Pro Ala Ser Arg Glu Leu Val Val Ser Tyr Val
            355                 360                 365

Asn Val Asn Met Gly Leu Lys Ile Arg Gln Leu Leu Trp Phe His Ile
370                 375                 380

Ser Cys Leu Thr Phe Gly Arg Glu Thr Val Leu Glu Tyr Leu Val Ser
385                 390                 395                 400

Phe Gly Val Trp Ile Arg Thr Pro Pro Ala Tyr Arg Pro Pro Asn Ala
                405                 410                 415

Pro Ile Leu Ser Thr Leu Pro Glu Thr Thr Val Val His His His His
            420                 425                 430

His His

<210> SEQ ID NO 20
<211> LENGTH: 453
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (448)..(453)
<223> OTHER INFORMATION: optionally absent

<400> SEQUENCE: 20

Met Gln Leu Phe Pro Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Ser Asn Leu Glu Asp Pro Ala Ser Arg Glu
            100                 105                 110

Leu Val Val Ser Tyr Val Asn Val Asn Met Gly Leu Lys Ile Arg Gln
```

```
                    115                 120                 125
Leu Leu Trp Phe His Ile Ser Cys Leu Thr Phe Gly Arg Glu Thr Val
130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Gly Gly Gly Gly Ser Gly Gly Gly Ser Gly Gly Gly Gly
            180                 185                 190

Ser Gly Gly Gly Gly Ser Asp Ile Gln Met Thr Gln Ser Pro Ala Ser
            195                 200                 205

Leu Ser Ala Ser Val Gly Glu Thr Val Thr Ile Thr Cys Arg Ala Ser
210                 215                 220

Glu Lys Ile Tyr Ser Tyr Leu Ala Trp Tyr Gln Gln Lys Gln Gly Lys
225                 230                 235                 240

Ser Pro Gln Leu Leu Val Tyr Asn Ala Lys Thr Leu Ala Glu Gly Val
                245                 250                 255

Pro Ser Arg Phe Ser Val Ser Gly Ser Gly Thr Gln Phe Ser Leu Arg
            260                 265                 270

Ile Asn Ser Leu Gln Pro Glu Asp Phe Gly Thr Tyr Tyr Cys Gln His
            275                 280                 285

His Phe Gly Ser Pro Arg Thr Phe Gly Gly Gly Thr Lys Leu Glu Ile
290                 295                 300

Lys Asp Leu Gly Gly Gly Gly Ser Gly Gly Gly Gly Ser Gly Gly Gly
305                 310                 315                 320

Gly Ser Gly Gly Gly Ser Thr Gly Glu Val Gln Leu Gln Gln Ser
                325                 330                 335

Gly Pro Glu Leu Val Lys Pro Gly Ala Ser Met Lys Ile Ser Cys Lys
            340                 345                 350

Ala Ser Gly Tyr Ser Phe Thr Gly Tyr Thr Met Asn Trp Val Lys Gln
            355                 360                 365

Ser His Gly Lys Thr Leu Glu Trp Ile Gly Leu Ile Asn Pro Tyr Asn
370                 375                 380

Gly Val Thr Ser Tyr Asn Gln Lys Phe Lys Asp Lys Ala Thr Leu Thr
385                 390                 395                 400

Val Asp Lys Ser Ser Ser Thr Ala Tyr Met Glu Leu Leu Ser Leu Thr
                405                 410                 415

Ser Glu Asp Ser Ala Ile Tyr Tyr Cys Ala Arg Asp Tyr Asn Tyr Asp
            420                 425                 430

Tyr Phe Asp Tyr Trp Gly Gln Gly Thr Thr Leu Thr Val Ser Ser His
            435                 440                 445

His His His His
    450

<210> SEQ ID NO 21
<211> LENGTH: 434
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (429)..(434)
<223> OTHER INFORMATION: optionally absent

<400> SEQUENCE: 21
```

```
Ser Lys Leu Cys Leu Gly Trp Leu Trp Gly Met Asp Ile Asp Pro Tyr
1               5                   10                  15

Lys Glu Phe Gly Ala Ser Val Glu Leu Leu Ser Phe Leu Pro Ser Asp
            20                  25                  30

Phe Phe Pro Ser Ile Arg Asp Leu Leu Asp Thr Ala Ser Ala Leu Tyr
        35                  40                  45

Arg Glu Ala Leu Glu Ser Pro Glu His Cys Ser Pro His His Thr Ala
50                  55                  60

Leu Arg Gln Ala Ile Leu Cys Trp Gly Glu Leu Met Asn Leu Ala Thr
65                  70                  75                  80

Trp Val Gly Ser Asn Leu Glu Asp Pro Ala Ser Arg Glu Leu Val Val
                85                  90                  95

Ser Tyr Val Asn Val Asn Met Gly Leu Lys Ile Arg Gln Leu Leu Trp
                100                 105                 110

Phe His Ile Ser Cys Leu Thr Phe Gly Arg Glu Thr Val Leu Glu Tyr
            115                 120                 125

Leu Val Ser Phe Gly Val Trp Ile Arg Thr Pro Pro Ala Tyr Arg Pro
        130                 135                 140

Pro Asn Ala Pro Ile Leu Ser Thr Leu Pro Glu Thr Thr Val Val Gly
145                 150                 155                 160

Gly Gly Gly Ser Gly Gly Gly Ser Gly Gly Gly Ser Gly Gly
                165                 170                 175

Gly Gly Ser Asp Ile Gln Met Thr Gln Ser Pro Ala Ser Leu Ser Ala
            180                 185                 190

Ser Val Gly Glu Thr Val Thr Ile Thr Cys Arg Ala Ser Glu Lys Ile
            195                 200                 205

Tyr Ser Tyr Leu Ala Trp Tyr Gln Gln Lys Gln Gly Lys Ser Pro Gln
        210                 215                 220

Leu Leu Val Tyr Asn Ala Lys Thr Leu Ala Glu Gly Val Pro Ser Arg
225                 230                 235                 240

Phe Ser Val Ser Gly Ser Gly Thr Gln Phe Ser Leu Arg Ile Asn Ser
                245                 250                 255

Leu Gln Pro Glu Asp Phe Gly Thr Tyr Tyr Cys Gln His His Phe Gly
            260                 265                 270

Ser Pro Arg Thr Phe Gly Gly Gly Thr Lys Leu Glu Ile Lys Asp Leu
        275                 280                 285

Gly Gly Gly Gly Ser Gly Gly Gly Gly Ser Gly Gly Gly Gly Ser Gly
                290                 295                 300

Gly Gly Gly Ser Thr Gly Glu Val Gln Leu Gln Gln Ser Gly Pro Glu
305                 310                 315                 320

Leu Val Lys Pro Gly Ala Ser Met Lys Ile Ser Cys Lys Ala Ser Gly
            325                 330                 335

Tyr Ser Phe Thr Gly Tyr Thr Met Asn Trp Val Lys Gln Ser His Gly
        340                 345                 350

Lys Thr Leu Glu Trp Ile Gly Leu Ile Asn Pro Tyr Asn Gly Val Thr
        355                 360                 365

Ser Tyr Asn Gln Lys Phe Lys Asp Lys Ala Thr Leu Thr Val Asp Lys
    370                 375                 380

Ser Ser Ser Thr Ala Tyr Met Glu Leu Leu Ser Leu Thr Ser Glu Asp
385                 390                 395                 400

Ser Ala Ile Tyr Tyr Cys Ala Arg Asp Tyr Asn Tyr Asp Tyr Phe Asp
            405                 410                 415

Tyr Trp Gly Gln Gly Thr Thr Leu Thr Val Ser Ser His His His His
```

His His

<210> SEQ ID NO 22
<211> LENGTH: 25
<212> TYPE: PRT
<213> ORGANISM: Artificial Sequence
<220> FEATURE:
<223> OTHER INFORMATION: Synthetic

<400> SEQUENCE: 22

```
His Met Lys Gln Leu Asp Val Glu Glu Leu Ser Asn Tyr His Leu Asn
1               5                   10                  15

Val Ala Arg Leu Lys Val Gly Glu Arg
            20                  25
```

<210> SEQ ID NO 23
<211> LENGTH: 33
<212> TYPE: PRT
<213> ORGANISM: Artificial Sequence
<220> FEATURE:
<223> OTHER INFORMATION: Synthetic

<400> SEQUENCE: 23

```
Gly Val Thr Gln Leu Met Arg Glu Met Leu Gln Leu Ile Lys Phe Gln
1               5                   10                  15

Phe Ser Leu Asn Tyr Gln Glu Glu Ser Leu Ser Tyr Gln Arg Leu Val
            20                  25                  30

Thr
```

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

```
Glu Val Ser Ala Leu Glu Lys
1               5
```

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

```
Lys Val Ser Ala Leu Lys Glu
1               5
```

<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

```
Ser Lys Leu Cys Leu Gly Trp Leu Trp Gly Met Asp Ile Asp Pro
1               5                   10                  15
```

<210> SEQ ID NO 27

```
<211> LENGTH: 15
<212> TYPE: PRT
<213> ORGANISM: Artificial Sequence
<220> FEATURE:
<223> OTHER INFORMATION: Synthetic

<400> SEQUENCE: 27

Leu Gly Trp Leu Trp Gly Met Asp Ile Asp Pro Tyr Lys Glu Phe
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Trp Gly Met Asp Ile Asp Pro Tyr Lys Glu Phe Gly Ala Ser Val
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Ile Asp Pro Tyr Lys Glu Phe Gly Ala Ser Val Glu Leu Leu Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Lys Glu Phe Gly Ala Ser Val Glu Leu Leu Ser Phe Leu Pro Ser
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Ala Ser Val Glu Leu Leu Ser Phe Leu Pro Ser Asp Phe Phe Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Leu Leu Ser Phe Leu Pro Ser Asp Phe Phe Pro Ser Ile Arg Asp
1               5                   10                  15

<210> SEQ ID NO 33
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 33

Leu Pro Ser Asp Phe Phe Pro Ser Ile Arg Asp Leu Leu Asp Thr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Phe Phe Pro Ser Ile Arg Asp Leu Leu Asp Thr Ala Ser Ala Leu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Ile Arg Asp Leu Leu Asp Thr Ala Ser Ala Leu Tyr Arg Glu Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Leu Asp Thr Ala Ser Ala Leu Tyr Arg Glu Ala Leu Glu Ser Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic

<400> SEQUENCE: 37

Ser Ala Leu Tyr Arg Glu Ala Leu Glu Ser Pro Glu His Cys Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Arg Glu Ala Leu Glu Ser Pro Glu His Cys Ser Pro His His Thr
1               5                   10                  15

<210> SEQ ID NO 39
<211> LENGTH: 15
<212> TYPE: PRT
```

<213> ORGANISM: Artificial Sequence
<220> FEATURE:
<223> OTHER INFORMATION: Synthetic

<400> SEQUENCE: 39

Glu Ser Pro Glu His Cys Ser Pro His His Thr Ala Leu Arg Gln
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

His Cys Ser Pro His His Thr Ala Leu Arg Gln Ala Ile Leu Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

His His Thr Ala Leu Arg Gln Ala Ile Leu Cys Trp Gly Glu Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

Leu Arg Gln Ala Ile Leu Cys Trp Gly Glu Leu Met Asn Leu Ala
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic

<400> SEQUENCE: 43

Ile Leu Cys Trp Gly Glu Leu Met Asn Leu Ala Thr Trp Val Gly
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

Gly Glu Leu Met Asn Leu Ala Thr Trp Val Gly Ser Asn Leu Glu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Asn Leu Ala Thr Trp Val Gly Ser Asn Leu Glu Asp Pro Ala Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic

<400> SEQUENCE: 46

Trp Val Gly Ser Asn Leu Glu Asp Pro Ala Ser Arg Glu Leu Val
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Asn Leu Glu Asp Pro Ala Ser Arg Glu Leu Val Val Ser Tyr Val
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48

Pro Ala Ser Arg Glu Leu Val Val Ser Tyr Val Asn Val Asn Met
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Glu Leu Val Val Ser Tyr Val Asn Val Asn Met Gly Leu Lys Ile
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic

<400> SEQUENCE: 50

Ser Tyr Val Asn Val Asn Met Gly Leu Lys Ile Arg Gln Leu Leu
1               5                   10                  15

<210> SEQ ID NO 51
<211> LENGTH: 15
<212> TYPE: PRT
<213> ORGANISM: Artificial Sequence
<220> FEATURE:

```
<223> OTHER INFORMATION: Synthetic

<400> SEQUENCE: 51

Val Asn Met Gly Leu Lys Ile Arg Gln Leu Leu Trp Phe His Ile
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Leu Lys Ile Arg Gln Leu Leu Trp Phe His Ile Ser Cys Leu Thr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic

<400> SEQUENCE: 53

Gln Leu Leu Trp Phe His Ile Ser Cys Leu Thr Phe Gly Arg Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic

<400> SEQUENCE: 54

Phe His Ile Ser Cys Leu Thr Phe Gly Arg Glu Thr Val Leu Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic

<400> SEQUENCE: 55

Cys Leu Thr Phe Gly Arg Glu Thr Val Leu Glu Tyr Leu Val Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Gly Arg Glu Thr Val Leu Glu Tyr Leu Val Ser Phe Gly Val Trp
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 57

Val Leu Glu Tyr Leu Val Ser Phe Gly Val Trp Ile Arg Thr Pro
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

Leu Val Ser Phe Gly Val Trp Ile Arg Thr Pro Pro Ala Tyr Arg
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Gly Val Trp Ile Arg Thr Pro Pro Ala Tyr Arg Pro Pro Asn Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic

<400> SEQUENCE: 60

Arg Thr Pro Pro Ala Tyr Arg Pro Pro Asn Ala Pro Ile Leu Ser
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Ala Tyr Arg Pro Pro Asn Ala Pro Ile Leu Ser Thr Leu Pro Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic

<400> SEQUENCE: 62

Pro Asn Ala Pro Ile Leu Ser Thr Leu Pro Glu Thr Thr Val Val
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 63

Ala Asp Phe Leu Tyr Ile Glu Ala His Asp Gly Trp
1               5                   10
```